United States Patent [19]
Schinstine et al.

[11] Patent Number: 5,843,431
[45] Date of Patent: Dec. 1, 1998

[54] CONTROLLING PROLIFERATION OF CELLS BEFORE AND AFTER ENCAPSULATION IN A BIOARTIFICIAL ORGAN BY GENE TRANSFORMATION

[75] Inventors: Malcolm Schinstine, Ben Salem, Pa.; Molly S. Shoichet, Toronto, Canada; Frank T. Gentile, Warwick; Joseph P. Hammang, Barrington, both of R.I.; Laura M. Holland, Horsham, Pa.; Brian M. Cain, Everett; Edward J. Doherty, Mansfield, both of Mass.; Shelley R. Winn, Smithfield, R.I.; Patrick Aebischer, Lutry, Switzerland

[73] Assignee: CytoTherapeutics, Inc.

[21] Appl. No.: 432,698

[22] Filed: May 9, 1995

Related U.S. Application Data

[63] Continuation-in-part of Ser. No. 279,773, Jul. 20, 1994.
[51] Int. Cl.$^6$ ............ A61K 48/00; C12N 11/00; C12N 5/00; C12N 11/10
[52] U.S. Cl. ............ 424/93.21; 435/172.3; 435/174; 435/178; 435/377; 435/382; 435/395; 424/93.7; 424/422
[58] Field of Search ............ 435/174, 178, 435/172.3, 240.7, 240.22, 240.23, 240.24, 240.241, 240.242, 240.243, 377, 382, 395; 424/93.21, 93.7, 422

[56] References Cited

U.S. PATENT DOCUMENTS

| | | | |
|---|---|---|---|
| 4,391,909 | 7/1983 | Lim | 435/178 |
| 4,402,694 | 9/1983 | Ash et al. | 404/891 |
| 4,489,796 | 12/1984 | Kallok | 604/449 |
| 4,495,288 | 1/1985 | Jarvis, Jr. et al. | 435/241 |
| 4,829,000 | 5/1989 | Kleinman et al. | 435/240.23 |
| 5,002,661 | 3/1991 | Chick et al. | 210/192 |
| 5,049,493 | 9/1991 | Khosa et al. | 435/69.1 |
| 5,082,670 | 1/1992 | Gage et al. | 424/520 |
| 5,106,627 | 4/1992 | Aebischer et al. | 424/424 |
| 5,156,844 | 10/1992 | Aebischer et al. | 424/424 |
| 5,158,881 | 10/1992 | Aebischer et al. | 435/182 |
| 5,182,111 | 1/1993 | Aebischer et al. | 424/424 |
| 5,250,414 | 10/1993 | Schwab et al. | 435/7.72 |
| 5,283,187 | 2/1994 | Aebischer et al. | 435/182 |
| 5,284,761 | 2/1994 | Aebischer et al. | 435/182 |

FOREIGN PATENT DOCUMENTS

| | | |
|---|---|---|
| 4123629 A | 2/1992 | Germany . |
| 2178447 | 2/1987 | United Kingdom . |
| WO 89/09816 | 10/1989 | WIPO . |
| WO 90/15863 | 12/1990 | WIPO . |
| WO 91/00119 | 1/1991 | WIPO . |
| WO 91/09939 | 7/1991 | WIPO . |
| WO 91/13150 | 9/1991 | WIPO . |
| WO 92/03536 | 3/1992 | WIPO . |
| 9195 | 11/1992 | WIPO . |
| WO 93/00127 | 1/1993 | WIPO . |
| WO 93/00128 | 1/1993 | WIPO . |
| WO 93/01275 | 1/1993 | WIPO . |
| WO 93/03768 | 3/1993 | WIPO . |
| WO 93/03901 | 3/1993 | WIPO . |
| WO 93/14790 | 8/1993 | WIPO . |
| WO 93/21902 | 11/1993 | WIPO . |
| WO 93/22427 | 11/1993 | WIPO . |
| WO 93/23431 | 11/1993 | WIPO . |
| WO 94/01129 | 1/1994 | WIPO . |
| WO 94/03199 | 2/1994 | WIPO . |
| WO 94/29442 | 12/1994 | WIPO . |
| WO 95/28166 | 10/1995 | WIPO . |

OTHER PUBLICATIONS

Farghali et al., The concept of Applicaiton of Immobilized and Perfused Mammalian cells (a bioreactor model) in biomedical research, *Physiological Research*, 43, pp. 117–120 (1994).

Adhya, Sankar, et al., "Promoter resurrection by activators—a minireview," *Gene*, 132, pp. 1–6 (1993).

Arnheiter, Heinz, et al., "Transgenic Mice with Intracellular Immunity to Influenza Virus," *Cell*, 62, pp. 51–61 (1990).

Aulthouse, Amy Lynn, et al., "Expression of the Human Chondrocyte Phenotype In Vitro," *In Vitro Cellular & Developmental Biology*, 25, pp. 659–658 (1989).

Baetge, E. Edward, et al., "Complete Nucleotide and Deduced Amino Acid Sequence of Bovine Phenylethanolamine N–methyltransferase: Partial Amino Acid Homology With Rat Tyrosine Hydroxylase," *Proc. Natl. Acad. Sci. USA*, 83, pp. 5454–5458 (1986).

(List continued on next page.)

*Primary Examiner*—David M. Naff
*Attorney, Agent, or Firm*—Ivor R. Elrifi; Mintz, Levin

[57] ABSTRACT

Methods and compositions are provided for controlling cell distribution within an implantable bioartificial organ by exposing the cells to a treatment that inhibits cell proliferation, promotes cell differentiation, or affects cell attachment to a growth surface within the bioartificial organ. Such treatments include (1) genetically manipulating cells, (2) exposing the cells to a proliferation-inhibiting compound or a differentiation-inducing compound or removing the cells from exposure to a proliferation-stimulating compound or a differentiation-inhibiting compound; exposing the cells to irradiation, and (3) modifying a growth surface of the bioartificial organ with extracellular matrix molecules, molecules affecting cell proliferation or adhesion, or an inert scaffold, or a combination thereof. These treatments may be used in combination. Cells can be transformed with a proliferation-promoting gene such as the oncogene, SV40, linked to a regulatable promoter such as the Mx1 promoter, the promotor is activated in vitro to express the gene to result in cell proliferation, and the promotor is inactivated before or after insertion of the cells in the bioartificial organ to inhibit expression of the gene to reduce or stop cell proliferation in vivo. The promoter can be reactivated in vivo to again express the gene to result in further cell proliferation. The gene may be a proliferation-suppressing gene such as p53 gene or RB gene, or a differentiation-inducing gene such as high mobility group chromosomal protein 14. Inhibiting gene expression in vitro causes cell proliferation, and inducing gene expression reduces or stops cell proliferation in vivo.

10 Claims, 5 Drawing Sheets

OTHER PUBLICATIONS

Baringa, Marcia, "Knockout Mice: Round Two," *Science*, 265, pp. 26–28 (1994).

Baron–Van Evercooren, A., et al., "Schwann Cell Differentiation in vitro: Extracellular Matrix Deposition and Interaction," *Dev. Neurosci.*, 8, pp. 182–196 (1886).

Blau, Helen M., et al., "Myoblasts in Pattern Formation and Gene Therapy," *Trends in Genetics*, 9, pp. 269–274 (1993).

Bohak, Z., et al., "Novel Anchorage Matrices for Suspension Culture of Mammalian Cells," *Biopolymers*, 26, pp. S205–S213 (1987).

Brenner, Michael, et al., "GFAP Promoter Directs Astrocyte-specific Expression in Transgenic Mice," *The Journal of Neuroscience*, 14, pp. 1030–1037 (1994).

Brinster et al., "Factors Affecting the Efficiency of Introducing Foreign DNA into Mice by Microinjecting Eggs," *Proc. Natl. Acad. Sci. USA*, 82, pp. 4438–4442 (1985).

Cabasso, Israel, "Hollow–Fiber Membranes," *Encyclopedia of Chemical Technology* (Kirk–Othmer, ed.), pp. 492–517 (1980).

Carbonetto, Salvatore, "Ch. 15: Laminin Receptors: From PC12 Cells to PNS," *Brain Repair* (Björklund, Aguayo and Ottoson, eds.), pp. 185–197 (1990).

Celtrix Laboratories, "Vitrogen 100®: Purified Collagen for Cell Culture and Biochemistry" (Product Information Memorandum), Celtrix Laboratories, Palo Alto, CA (1991).

Cepko, Connie, "Retrovirus Vectors and Their Applications in Neurobiology," *Neuron*, 1, 345–453 (1988).

Chang, P.L., et al., "Delivery of Recombinant Gene Products with Microencapsulated Cells In Vivo," *Human Gene Therapy*, 4, pp. 433–440 (1993).

Chu, C.H., and A.M. Tolkovsky, "Alternative Adrenal Chromaffin Cell Fates Induced by Basic Fibroblast Growth Factor or Cyclic AMP In Vitro Depend on a Collaboration With The Growth Substrate," *Neuroscience*, 59, pp. 43–54 (1994).

Collaborative Research Incorporated, "CR–Laminin and CR–Anti–Laminin" (Product Information Memorandum), Collaborative Research, Inc., Bedford, MA (1987).

Collaborative Research Incorporated, "Basement Membrane Matrigel™" (Product Specification Sheet), Collaborative Research, Inc., Bedford, MA (1991).

Collagen Biomedical, "Collagen Test Implant Physician Package Insert," (Product Information Literature), Collagen Biomedical, Palo Alto, CA (1992).

Collagen Biomedical, "Zyderm® Collagen and Zyderm® Explained," (Product Information Memorandum), Collagen Biomedical, Palo Alto, CA (1992).

Collagen Biomedical, "Zyderm® Collagen Implant Physician Package Insert," (Product Literature), Collagen Biomedical, Palo Alto, CA (1992).

Collagen Biomedical, "Zyplast® Implant Physician Package Insert," (Product Literature), Collagen Biomedical, Palo Alto, CA (1992).

Crouch, Gary D., et al., "Ara–C Treatment Leads to Differentiation and Reverses the Transformed Phenotype in a Human Rhabdomyosarcoma Cell Line," *Experimental Cell Research*, 204, pp. 210–216 (1993).

Datta, Dipak B., "Keeping In Touch: The Adhesion Reactions of the Cell Membrane," *A Comprehensive Introduction to Membrane Biochemistry*, pp. 231–256 (1987).

de Bruine, Adriaan P., et al., "Extracellular Matrix Components Induce Endocrine Differentiation in Vitro in NCI–H716 Cells," *American Journal of Pathology*, 142, pp. 773–782 (1993).

De Loecker, William, et al., "Effects of Sodium Ascorbate (Vitamin C) and 2-Methyl-1,4-naphthoquinone (Vitamin $K_3$) Treatment on Human Tumor Cell Growth in Vitro. II. Synergism with Combined Chemotherapy Action," *Anticancer Research*, 13, pp. 103–106 (1993).

Edgar, David, "Neuronal aminin receptors," *TINS*, 12, pp. 248–251 (1989).

El–Deiry, Wafik S., et al., "*WAF1*, a Potential Mediator of p53 Tumor Suppression," *Cell*, 75, pp. 817–825 (1993).

End, Peter, and Jurgen Engel, "Multidomain Proteins of the Extracellular Matrix and Cellular Growth," *Receptors for Extracellular Matrix* (McDonald, J. and Mecham,R., ed.), pp. 79–129 (1991).

Epstein–Baak, Ruth, et al., "Inducible Transformation of Cells from Transgenic Mice Expressing SV40 under lac Operon Control," *Cell Growth and Differentiation*, 3, pp. 127–134 (1992).

Fattaey, H.K., et al., "Modulation of Growth–Related Gene Expression and Cell Cycle Synchronization by a Sialoglycopeptide Inhibitor," *Experimental Cell Research*, 194, pp. 62–68 (1991).

Fattaey, Heideh, et al., "Inhibition of DNA Synthesis and Cell Division by a Cell Surface Sialoglycopeptide," *Journal of Cellular Physiology*, 139, pp. 269–274 (1989).

Fujiyama, C., et al., "Influence of Extracellular Matrix on the Proliferation and Differentiation of Adrenocortical Cells in Culture," *Path. Res. Pract.*, 189, pp. 1205–1214 (1993).

Galli, Maria C., et al., "The Biology of Stem Cell Factor, a New Hematopoietic Growth Factor Involved in Stem Cell Regulation," *Int. J. of Clin. Lab. Res.*, 23, pp. 70–77 (1993).

Gash, D.M., et al., "Amitotic Neuroblastoma Cells Used for Neural Implants in Monkeys," *Science*, 233, pp. 1420–1422 (1986).

Gonos, Efstathios S., and Demetrios A. Spandidos, "Oncogenes in Cellular Immortalisation and Differentiation (Review)," *Anticancer Research*, 13, pp. 1117–1122 (1993).

Grabham, Peter W., et al., "Vibronectin Is the Major Serum Protein Essential for NGF–Mediated Neurite Outgrowth from PC12 Cells," *Experimental Cell Research*, 202, pp. 337–344 (1992).

Graf, Jeannette, et al., "A Pentapeptide from the Laminin β1 Chain Mediates Cell Adhesion and Binds the 67 000 Laminin Receptor," *Biochemistry*, 26, pp. 6896–6900 (1987).

Graf, Jeannette, et al., "Identification of an Amino Acid Sequence in Laminin Mediating Cell Attachment, Chemotaxis, and Receptor Binding," *Cell*, 48, pp. 989–996 (1987).

Gu, Hua, et al., "Deletion of a DNA Polymerase β Gene Segment in T Cells Using Cell Type–Specific Gene Targeting," *Science*, 265, pp. 103–106 (1994).

Gumbiner, Barry M., "Proteins Associated with the Cytoplasmic Surface of Adhesion Molecules," *Neuron*, 11, pp. 551–564 (1993).

Hammang, Joseph P., et al., "Immortalized Neuronal and Neuroendocrine Cell Lines by Targeted Oncogenesis in Transgenic Mice Using the PNMT Promoter," *Neuroprotocols: A Companion to Methods in Neurosciences*, 3, pp. 176–183 (1993).

Hannan, G.N., et al., "An engineered PGK promoter and Lac operator–repressor system for the regulation of gene expression in mammalian cells," *Gene*, 130, pp. 233–239 (1993).

Hoyle, Gary W., et al., "Expression of NGF in Sympathetic Neurons Leads to Excessive Axon Outgrowth from Ganglia but Decreased Terminal Innervation within Tissues," *Neuron*, 10, pp. 1019–1034 (1993).

Hubbell, Jeffrey A., et al., "Surface–grafted Cell–binding Peptides in Tissue Engineering of the Vascular Graft," *Annals New York Academy of Sciences*, 665, pp. 253–258 (1992).

Hug, Hubert, et al., "Organization of the Murine Mx Gene and Characterization of Its Interferon– and Virus–Inducible Promoter," *Molecular and Cellular Biology*, 8, pp. 3065–3079 (1988).

HyClone Laboratories, "CultiSpher–G" (Product Information Memorandum), HyClone Laboratories, Logan, UT (no date).

HyClone Laboratories, "CultiSpher–GL" (Product Information Memorandum), HyClone Laboratories, Logan, UT (no date).

Ito, Yoshihiro, et al., "Materials for Enhancing Cell Adhesion By Immobilization of Cell–Adhesive Peptide," *Journal of Biomedical Materials Research*, 25, pp. 1325–1337 (1991).

Iwamoto, Yukihide, et al., "YIGSR, a Synthetic Laminin Pentapeptide, Inhibits Experimental Metastasis Formation," *Science*, 238, pp. 1132–1134 (1987).

Johnson, Terry C., and Behrooz G. Sharifi, "Abrogation of the Mitogenic Activity of Bombesin by a Cell Surface Sialoglycopeptide Growth Inhibitor," *Biochemical and Biophysical Research Communications*, 161, pp. 468–474 (1989).

Jucker, M., et al., "Fetal Rats Septal Cells Adhere to and Extend Processes on Basement Membrane, Laminin, and a Synthetic Peptide the Laminin A Chain Sequence," *J. Neurosic. Res.*, 28, 507–517 (1991).

Kleinman, Hynda K., et al., "The Role of Laminin in Basement Membranes and in the Growth, Adhesion, and Differentiation of Cells," *The Role of Extracellular Matrix in Development*, pp. 123–143 (1984).

Kleinman, Hynda K., and Benjamin S. Weeks, "The Neural Cell Response to Laminin: Active Sites, Receptors, and Intracellular Signals," *Comments Developmental Neurobiology*, 1, pp. 251–266 (1991).

Lakshmanarao, S.S., et al., "Identification of a Cell Surface Component of Swiss 3T3 Cells Associated with an Inhibition of Cell Division," *Experimental Cell Research*, 195, pp. 412–415 (1991).

Land, Hartmut, et al., "Tumorigenic Conversion of Primary Embryo Fibroblasts Requires At Least Two Cooperating Oncogenes," *Nature*, 304, pp. 596–602 (1983).

Leung, Ping. Y., et al., "Cytotoxic Effect of Ascorbate and its Derivatives on Cultured Malignant and Nonmalignant Cell Lines," *Anticancer Research*, 13, pp. 475–480 (1993).

Lim, F., et al., "Microencapsulated Islets as Bioartificial Endocrine Pancreas," *Science*, 210, pp. 908–910 (1980).

Liu, Hong–Wen, et al., "Expression of Human Factor IX by Microencapsulate Recombinant Fibroblasts," *Human Gene Therapy*, 4, pp. 291–301 (1993).

Massia, Stephen P., and Jeffrey A. Hubbell, "Covalent Surface Immobilization of Arg–Gly–Asp– and Try–Ile–Gly– Ser–Arg–Containing Peptides to Obtain Well–Defined Cell–Adhesive Substrates," *Analytical Biochemistry*, 187, pp. 292–301 (1990)

Matsuda, Takehisa, et al., "Development of a Novel Artificial Matrix with Cell Adhesion Peptides for Cell Culture and Artificial and Hybrid Organs," *Trans. Am. Soc. Artif. Intern. Organs*, 35, pp. 677–679 (1989).

Matsushima, Hiroshi, and Emil Bogenmann, "Modulation of Neuroblastoma Cell Differentiation by the Extracellular Matrix," *Int. J. Cancer*, 51, pp. 727–732 (1992).

Matuoka et al., "Heparan Sulfate Enhances Growth of Transformed Human Cells," *Cell Structure and Function*, 9, p. 357 (1984).

Messing, Albee, et al., "Hypomyelinating Peripheral Neuropathies and Schwannomas in Transgeninc Mice Expressing SV40 T–Antigen," *The Journal of Neuroscience*, 14, pp. 3533–3539 (1994).

Mitchell, J.B., et al., "Dose–Rate Effects in Mammalian Cells in Culture," *Radiat. Res.*, 79, pp. 537–551 (1979).

Murata, Jun, et al., "Inhibitory Effect of a Synthetic Polypeptide, Poly(Tyr–Ile–Gly–Ser–Arg), On the Metastatic Formation of Malignant Tumour Cells," *Int. J. Biol. Macromol.*, 11, pp. 97–99 (1989).

Neckers, Len, and Luke Whitesell, "Antisense Technology: Biological Utility and Practical Considerations," *Am. J. Physiol.*, 265, pp. L1–L12 (1993).

Otonkoski, Timo, et al., "Nicotinamide Is a Potent Inducer of Endocrine Differentiation in Cultured Human Fetal Pancreatic Cells," *J. Clin. Invest.*, 92, pp. 1459–1466 (1993).

Pash, James M., et al., "Aberrant Expression of High Mobility Group Chromosomal Protein 14 Affects Cellular Differentiation," *The Journal of Biological Chemistry*, 268, pp. 13632–13638 (1993).

Penttienen, Risto P., et al., "Transforming Growth Factor β Increases mRNA for Matrix Proteins Both in the Presence and in the Absence of Changes in mRNA Stability," *Proc. Natl. Acad. Sci. USA*, 85, pp. 1105–1108 (1988).

Phillips, Charlotte L., et al., "Ascorbic Acid and Transforming Growth Factor–β1 Increase Collagen Biosynthesis via Different Mechanisms: Coordiante Regulation of Proα1(I) and Proα1(III) Collagens," *Archives of Biochemistry and Biophysics*, 295, pp. 397–403 (1992).

Pierschbacher, Michael D., and Erkki Ruoslatiti, "Cell Attachment Activity of Fibronectin Can Be Duplicated By Small Synthetic Fragments of the Molecule," *Science*, 309, pp. 30–33 (1984).

Pleasure, Samuel, et al., "Pure, Postmitotic, Polarized Human Neurons Derived from NTera 2 Cells Provide a System for Expressing Exogenous Proteins in Terminally Differentiated Neurons," *The Journal of Neuroscience*, 12, pp. 1802–1815 (1992).

Prystowsky et al., "Inhibition of Ornithine Decarboxylase Activity and Cell Proliferation by Ultraviolet β Radiation in EGF–Stimulated Cultured Human Epidermal Keratinocytes," *J. Invest. Dermat.*, 101, pp. 54–58 (1993).

Radvanyi, Francois, et al., "Pancreatic β Cells Cultured from Individual Preneoplastic Foci in a Multistage Tumorigenesis Pathway: a Potentially General Technique for Isolating Physiologically Representative Cell Lines," *Molecular and Cellular Biology*, 13, pp. 4223–4232 (1993).

Ray, Jasodhara, et al., "Proliferation, Differentiation, and Long–Term Culture of Primary Hippocampal Neurons," *Proc. Natl. Acad. Sci. USA*, 90, pp. 3602–3606 (1993).

Reemay, Inc., "Reemay® Spunbonded Polyester," pp. 1–20 (Product Information Literature), Reemay, Inc., Old Hickory, TN.

Reynolds, Brent A., et al., "A Multipotent EGF–Responsive Striatal Embryonic Progenitor Cell Produces Neurons and Astrocytes," *The Journal of Neuroscience,* 12, pp. 4565–4574 (1992).

Richards, L.J. et al., "De novo Generation of Neuronal Cells From The Adult Mouse Brain," *Proc. Natl. Acad. Sci. USA,* 89, pp. 8591–8595 (1992).

Ron, David, "Inducible Growth Arrest: New Mechanistic Insights," *Proc. Natl. Acad. Sci. USA,* 91, pp. 1985–1986 (1994).

Ruoslahti, Erkki, and Michael D. Pierschbacher, "New Perspectives in Cell Adhesion: RGD and Integrins," *Science,* 238, pp. 491–497 (1987).

Ruoslahti, Erkki, and John C. Reed, "Anchorage Dependence, Integrins, and Apoptosis," *Cell,* 77, pp. 477–478 (1994).

Saiki, I., et al., "Antimetastic Effects of Synthetic Polypeptides Containing Repeated Structures of the Cell Adhesive Arg–Gly–Asp (RGD) and Tyr–Ile–Gly–Ser–Arg (YIGSR) Sequences," *Br. J. Cancer,* 60, pp. 722–728 (1989).

Sanes, Joshua R., "Extracellular Matrix Molecules That Influence Neural Development," *Ann. Rev. Neurosci.,* 12, pp. 491–516 (1989).

Schinstine, Malcolm, and Fred H. Gage, "Factors Affecting Proviral Expression in Primary Cells Grafted into the CNS," *Molecular and Cellular Approaches for the Treatment of Neurological Diseases* (S.G. Waxman, ed.), pp. 311–323 (1993).

Seliger, Barbara, et al., "Murine Gamma Interferon Inhibits v–mos–Induced Fibroblast Transformation via Down Regulation of Retroviral Gene Expression," *Journal of Virology,* 61, pp. 2567–2572 (1987).

Seliger, Barbara, et al., "Gamma Interferon Regulates Long Terminal Repeat–Controlled Oncogene Expression in Transformed Mouse Fibroblasts at the Level of mRNA Transcription," *Journal of Virology,* 62, pp. 619–621 (1988).

Seliger, Barbara, et al., "Tumor Necrosis Factor–α Affects LTR–Controlled Oncogene Expression in Transformed Mouse Fibroblasts at the Post–Transcriptional Level," *The Journal of Immunology,* 141, pp. 2138–2144 (1988).

Seliger, Barbara, et al., "Distinct Mechanisms of Interferon–Gamma and Tumor Necrosis Factor–Alpha Action in Oncogene–Transformed Mouse Fibroblasts," *Journal of Cellular Biochemistry,* 38, pp. 205–212 (1988).

Sharifi, Behrooz G., et al., "Cell Surface Interaction is Sufficient for the Biological Activity of a Bovine Sialoglycopeptide Inhibitor," *Biochemical and Biophysical Research Communications,* 134, pp. 1350–1357 (1986).

Sharifi, Behrooz G., et al., "Purification and Characterization of a Bovine Cerebral Cortex Cell Surface Sialoglycopeptide that Inhibits Cell Proliferation and Metabolism," *Journal of Neurochemistry,* 46, pp. 461–469 (1986).

Smalheiser, Neil R., et al., "Laminin As a Substrate for Retinal Axons In Vitro," *Dev. Brain Res.,* 12, pp. 136–140 (1984).

SoloHill Labs, Inc., SoloHill Labs, Inc., Ann Arbor, MI.

Stockdale, Frank E., et al., "Myoblasts, Satellite Cells, and Myoblast Transfer," *Myoblast Transfer Therapy* (R. Griggs and G. Karpati, eds.), pp. 7–11 (1990).

Sun, Anthony M., "Microencapsulation of Pancreatic Islet Cells: A Bioartificial Endocrine Pancreas," *Methods in Enzymology,* 137, pp. 575–580 (1988).

Tashiro, Ken–ichiro, et al., "A Synthetic Peptide Containing the IKVAV Sequence from the A Chain of Laminin Mediates Cell Attachment, Migration, and Neurite Outgrowth," *The Journal of Biological Chemistry,* 264, pp. 16174–16182 (1989).

Telios Pharmaceuticals, "Integrins: An Update on the Rapid Growth of Research Topics," in *ECM Connections,* a publication of Telios Pharmaceuticals, San Diego, CA (Jun. 1992).

Telios Pharmaceuticals, "PepTite–2000" (Product Information Memorandum), Telios Pharmaceuticals, San Diego, CA.

Temple, Sally, "Division and Differentiation of Isolated CNS Blast Cells in Microculture," *Nature,* 340, pp. 471–473 (1989).

Tomaselli, K.J., et al., "A Neuronal Cell Line (PC12) Expresses Two $\beta_1$–Class Integrins—$\alpha_1\beta_1$ and $\alpha_3\beta_1$—That Recognize Different Neurite Outgrowth–Promoting Domains in Laminin," *Neuron,* 5, pp. 651–662 (1990).

Toole–Simms, W.E., et al., "Effects of a Sialoglycopeptide on Early Events Associated With Signal Transduction," *Journal of Cellular Physiology,* 147, pp. 292–297 (1991).

Townsend Jr., Courtney M., et al, "Studies of Growth Regulation in a Neuroendocrine Cell Line," *Acta Oncologica,* 32, pp. 125–130 (1993).

Trosko, J.E., et al., "Minireview: Endogenous and Exogenous Modulation of Gap Junction Intercellular Communication: Toxicological and Pharmacological Implications," *Life Sciences,* 53, pp. 1–19 (1993).

Vehe, Richard K., et al., "Transcriptional Regulatory Elements for Constitutive and IFN–λ Inducible Expression of HLA–DRB1," *Transgene,* 1, pp. 59–66 (1993).

Weinberg, Robert, "Tumor Suppressor Genes," *Neuron,* 11, pp. 191–196 (1993).

Welsh, Michael, et al., "Genetic Factors of Importance for β–Cell Proliferation," *Diabetes/Metabolism Reviews,* 9, pp. 25–36 (1993).

Wollheim, Claes B., et al., "Establishment and Culture of Insulin–Secreting β Cell Lines," *Methods in Enzymology,* 192, pp. 223–235 (1990).

Yao, Shou–Nan, and Kotoku Kurachi, "Implanted Myoblasts Not Only Fuse With Myofibers But Also Survive As Muscle Precursor Cells," *Journal of Cell Science,* 105, pp. 957–963 (1993).

Yi, P.N., et al, "Relationship Between Mitotic Delay and the Minimum Dose Rate of X Irradiation Required To Stop Cell Proliferation," *Radiation Research,* 133, pp. 163–169 (1993).

CONTROLLING PROLIFERATION OF CELLS BEFORE AND AFTER ENCAPSULATION IN A BIOARTIFICIAL ORGAN BY GENE TRANSFORMATION

This is a continuation-in-part of copending U.S. application Ser. No. 08/279,773, filed Jul. 20, 1994, entitled "Methods and Compositions of Growth Control for Cells Encapsulated Within Bioartificial Organs."

FIELD OF THE INVENTION

This invention relates to methods and compositions for controlling growth of cells encapsulated in a bioartificial organ.

BACKGROUND OF THE INVENTION

Bioartificial organs "BAO" are devices which contain living cells and are designed to provide a needed metabolic function to a host.

The cells encapsulated in BAOs supply one or more biologically active molecules to the host that may be used to prevent or treat many clinical conditions, deficiencies, and disease states.

For example, BAOs containing insulin secreting cells may be used to treat diabetes. Similarly other diseases such as hypoparathyroidism and anemia may be treated by using cells which secrete parathyroid hormone and erythropoietin, respectively.

Bioartificial organs may also be used to supply biologically active molecules for the treatment or prevention of neurodegenerative conditions such as Huntington's disease, Parkinson's disease, Alzheimer's disease, and Acquired Immune Deficiency Syndrome-related dementia. Additionally, lymphokines and cytokines may also be supplied by BAOs to modulate the host immune system. Other biologically active molecules which may be provided by bioartificial organs include, catecholamines, endorphins, enkephalins, and other opioid or non-opioid peptides that are useful for treating pain. Enzymatic deficiencies may also be treated by using BAOs. Alternatively, the biologically active molecule may remove or eliminate deleterious molecules from the host. For example, a BAO may contain cells which produce a biologically active molecule that can be used to "scavenge" cholesterol from a host.

Various "macrocapsule" BAOs are known. See, e.g., Aebischer (U.S. Pat. No. 5,158,881), Dionne et al. (WO 92/03327), Mandel et al. (WO 91/00119), Aebischer (WO 93/00128). BAOs also include extravascular diffusion chambers, intravascular diffusion chambers, intravascular ultrafiltration chambers, and microcapsules. See, e.g., Lim et al., *Science* 210:908–910 (1980); Sun, A.M., *Methods in Enzymology* 137: 575–579 (1988); Dunleavy et al. (WO 93/03901) and Chick et al. (U.S. Pat. No. 5,002,661).

Because the cells encapsulated in the BAO provide the needed metabolic function, it is desirable that those cells optimally supply the biologically active molecule that effects that function. Typically, differentiated, non-dividing cells may be preferred over dividing cells for use in BAOs because they allow for the optimal production of the desired biologically active molecule. For example, many differentiated, non-dividing cells produce a greater quantity of a desired therapeutic protein than dividing cells because the expression of differentiation specific genes and cell division are thought to be antagonistic processes. Wollheim, "Establishment and Culture of Insulin-Secreting β Cell Lines," *Methods in Enzymology*, 192, p. 223–235 (1990). Cellular replication capacity decreases as cells differentiate. In many cases, proliferation and differentiation are mutually exclusive. Gonos, "Oncogenes in Cellular Immortalisation and Differentiation," 13, *Anticancer Research*, p. 1117 (1993).

The use of differentiated tissue is advantageous because the functional properties of tissue desired for incorporation into a BAO have most often been defined by the properties of differentiated tissue in vivo. Another advantage to the use of differentiated, non-dividing cells is that the cell number within the BAO will remain relatively constant. This, in turn, leads to more predictable results and stable dosage for the recipient host. Additionally, differentiated cells are better suited for use in BAOs which encapsulate more than one cell type secreting biologically active molecules. In such BAOs, if dividing cells are used, different cell types may grow at different rates, resulting in the overgrowth of one cell type. By using differentiated, non-dividing cells, the relative proportions of two or more synergistic cell types can be more readily controlled.

Although in many instances the use of differentiated cells is advantageous, there have been various problems associated with utilizing differentiated cells directly isolated from mammals.

First, there is the potential contamination of the isolated tissue which may require that the tissue taken from each animal be subjected to costly and time-consuming testing to assure that it is pathogen-free.

Second, tissue can be damaged during isolation due to the use of mechanical or enzymatic isolation procedures in the isolation process. The mechanical manipulations are not always easily standardized, resulting in variability between isolations.

Third, ischemia may occur during isolation causing tissue damage.

Fourth, reproducible yields may be difficult because of variations in tissue donors. For example, the age, sex, health, hormonal status of the source animal can affect the yield and quality of the tissue of interest.

Fifth, sometimes there is not enough source tissue to meet the projected demand for the BAO. This occurs for example, in a case where the source tissue comes from a small sized organ or where the ultimate need for tissue amounts is high. If the source of the isolated tissue is human, there is frequently a severe shortage of donor tissue.

Sixth, in some cases, it is desirable to genetically modify the cells used in the BAO. Non-dividing tissue to date has been difficult to genetically modify in vitro and the yields and properties of the modified cells may be uncertain. Thus, because of the foregoing problems, while the use of differentiated, non-dividing cells is desirable, a need exists for a method of producing and maintaining differentiated, non-dividing cells for encapsulation in BAOs.

Because of these problems, dividing cells and cell lines have been favored for use within BAOs to provide the needed biological function. One important advantage in using dividing cells is that such cells may be grown to large numbers in vitro and screened for pathogens and banked. This allows an almost unlimited supply of tissue for lower production costs. Selection schemes such as cell sorting or cloning may be applied to the cell bank to develop subpopulations with improved characteristics. Additionally, dividing cells and cell lines are more amenable to genetic engineering than differentiated, non-dividing cells. The ability to introduce heterologous recombinant DNA allows many new possibilities for the alteration of the function or phenotype of cells to be encapsulated in the BAO. This in turn provides for a greater diversity of therapeutic uses for BAOs.

However, as discussed supra, the disadvantages in encapsulating continuously dividing cells in a BAO include poor regulation of cell numbers in the device that may result in less predictability in production of the desired biologically active molecule.

While in most cases it may be desirable to limit or minimize cell growth within the BAO, in other cases, e.g., where the BAO is implanted in a "hostile" environment, it may be desirable to allow the cells to proliferate slowly to maintain cell numbers in the BAO.

There is another problem associated with encapsulating cells in general. A variety of cell types have cell adherent properties such that cells tend to adhere to each other and form dense agglomerations or aggregates, especially if there is no adequate substrate available for the cells. Such cell clusters may develop central necrotic regions due to the relative inaccessibility of nutrients and oxygen to cells embedded in the core, or due to the build up of toxic products within the core. The necrotic tissue may also release excess cellular proteins which unnecessarily flood the host with xeno-proteins or other factors which are detrimental to the surviving cells, e.g., factors which elicit a macrophage or other immune response. This problem may be exacerbated when cells are encapsulated in a BAO with a semipermeable membrane jacket because of diffusional constraints across the membrane. Often less oxygen and fewer host supplied nutrients are available within the BAO. In addition, waste products may accumulate in the BAO.

These dense cellular masses can form slowly into dense colonies of cell growth or form rapidly, upon the reassociation of freshly-dispersed cells or tissue mediated by cell-surface adhesion proteins. Cells or tissues with a high metabolic activity may be particularly susceptible to the effects of oxygen or nutrient deprivation, and die shortly after becoming embedded in the center of a large cell cluster. Many endocrine tissues, which normally are sustained by dense capillary beds, exhibit this behavior; islets of Langerhans appear to be particularly sensitive when encapsulated.

There is a need to have a method and composition for controlling the growth of encapsulated cells which combines the various advantages of both proliferating cells and differentiated, non-dividing cells. The present invention provides methods and compositions whereby cells can be proliferated and expanded indefinitely in vitro and where the balance between proliferation and differentiation can be controlled when the cells are encapsulated within the BAO so that the device performs in the desired manner. This invention thus allows regulation of the cell number within the BAO and may therefore provide improved regulation of the output level of the capsule. This invention also provides methods for controlling the growth of cells by controlling cell location within the BAO, thereby reducing the formation of undesirable necrotic cell cores in the BAO. Controlling the cell number and cell location within the BAO also provides the advantage of facilitating optimization of the BAO membrane and other device paramaters to the particular encapsulated cell type. This is because the required device characteristics are more readily determined for a fixed cell population than for a dividing cell population in the BAO. Additionally, long term delivery of biologically active molecules can be achieved.

SUMMARY OF THE INVENTION

The present invention addresses the foregoing problems by providing methods and compositions for controlling the distribution of cells (i.e. cell number or cell location in the BAO, or both) when encapsulated in a BAO. The methods and compositions of this invention include (1) methods and compositions for modification of the cells that are encapsulated within the BAO and (2) methods and compositions for modifying the growth surfaces within the BAO.

Methods and compositions for cellular manipulation include genetic alteration of the cells with a gene which encodes a product that influences cell proliferation or differentiation. The treatment may comprise providing a chemical compound or growth factor which inhibits proliferation or induces differentiation. Alternatively, the treatment may comprise removing from the growth medium a chemical compound or growth factor which stimulates proliferation or inhibits differentiation. The treatment may be before or after encapsulation in the BAO, preferably before encapsulation. Additionally, cell proliferation may be controlled by irradiation.

Methods and compositions for growth surface modification include coating at least one growth surface within the BAO with one or more extracellular matrix molecules ("ECM"). The ECMs may be coated directly onto the luminal surface or any inner support within the BAO, or onto microsphere carriers ("microcarriers"). Cells or cell-seeded microcarriers may additionally be suspended in a matrix material that physically inhibits cell proliferation. Further, the matrix material may be derivatized with chemical or peptide derivatives.

In addition, a growth surface of the BAO can be modified by chemical treatment to inhibit cell attachment or to enhance cell attachment to the BAO's luminal surface. Further, the growth surface can be modified by addition of an inert scaffold prior to cell loading. The scaffold physically inhibits cell outgrowth and provides additional sites for cell attachment. It is to be understood that the various methods and compositions for cell modification and for growth surface modification are not mutually exclusive and may be used in combination.

BRIEF DESCRIPTION OF THE DRAWINGS

FIG. 4A shows basal catecholamine release; FIG. 4B shows K$^+$-evoked catecholamine release. The abbreviations L-dopa, NEPI, epi, DOPAC, DA and HVA in the legend represent L-dopa, norepinephrine, epinephrine, dopac, dopamine, and homovanillic acid, respectively.

FIGS. 5A shows basal catecholamine release; FIG 5B shows K$^+$-evoked catecholamine release. The abbreviations L-dopa, NEPI, epi, DOPAC, DA and HVA in the legend represent L-dopa, norepinephrine, epinephrine, dopac, dopamine, and homovanillic acid, respectively.

DETAILED DESCRIPTION OF THE INVENTION

Definitions

Figure 1:
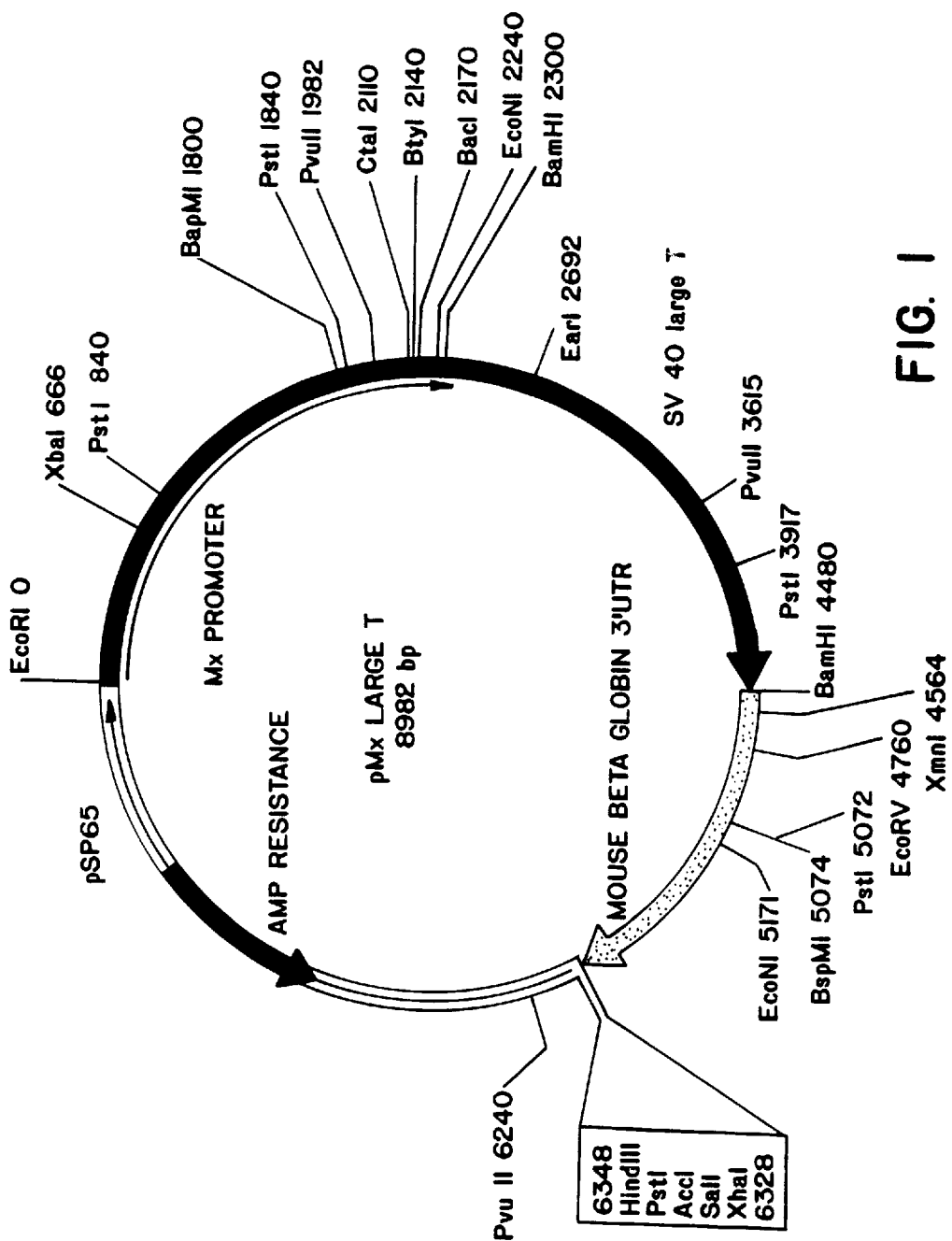
FIG. 1 depicts the plasmid map of a construct containing a 2.3 kb fragment of the murine Mx1 promoter fused to SV40 early region, followed by a BamH1-Xba1 fragment from mouse beta globin 3' untranslated region.

As used herein, a "bioartificial organ" or "BAO" is a device which may be designed for implantation into a host or which may be made to function extracorporeally and either be permanently or removably attached to a host. A BAO contains cells or living tissues which produce a biologically active molecule that has a therapeutic effect on the host. The BAO, upon implantation in a host recipient, should be biocompatible. Accordingly, the BAO should not elicit a detrimental host response sufficient to render it inoperable or not therapeutically useful. Such inoperability may occur, for example, by formation of a fibrotic structure around the capsule limiting diffusion of nutrients to the cells therein. Detrimental effects may also include rejection of the capsule or release of toxic or pyrogenic compounds (e.g. synthetic polymer by-products) from the BAO to surrounding host tissue.

BAOs comprising encapsulated cells may be constructed with immunoisolatory properties which hinder elements of the host immune system from entering the organ, thereby protecting the cells contained within the bioartificial organ from detrimental immune destruction. The use of a BAO increases the diversity of cell types that can be employed in therapy. In implanted BAOs, the devices, which may or may not be immunoisolatory, usually contain the cells or tissues producing a selected product within a semi-permeable physical barrier which will allow diffusion of nutrients, waste materials, and secreted products into surrounding host tissue and retain the contained cells, but minimize the deleterious effects of the cellular and molecular effectors of immunological rejection. Immunoisolatory properties, however, may not be necessary in all cases (e.g., if the cells are autologous or syngeneic to the host).

A "biologically active molecule" is one which (a) may function within the cell in which it is made or (b) may be expressed on the cell surface and affect the cell's interactions with other cells or biologically active molecules (e.g., a neurotransmitter receptor or cell adhesion molecule), or (c) may be released or secreted from the cell in which it is made and exert its effect on a separate target cell or target molecule in the host (e.g., a neurotransmitter, hormone, growth factor, or cytokine).

As used herein, unless otherwise specified, the term "cells" means cells in any form, including but not limited to cells retained in tissue, cell clusters, and individually isolated cells. The cells used in this invention produce at least one biologically active molecule.

Control of cell distribution within the BAO refers to control of the cell number in the BAO, control of the spatial location of cells within the BAO, or both.

A wide variety of cells may be used in this invention. These include well known, publicly available immortalized cell lines as well as dividing primary cell cultures. Examples of publicly available cell lines suitable for the practice of this invention include, L-6 cells, MDCK cells, LLC-PK cells, β-CH3 cells, C2 cells, by hamster kidney (BHK), Chinese hamster ovary (CHO), mouse fibroblast (L-M), NIH Swiss mouse embryo (NIH/3T3), African green monkey cell lines (including COS-a, COS-1, COS-6, COS-7, BSC-1, BSC-40, BMT-10 and Vero), rat adrenal pheochromocytoma (PC12), rat glial tumor cells (C6), RAJI (human lymphoma) cells, MOPC-31C mouse plasmacytoma cells, MN9D cells, MN9H cells, ripTAg transgenic mouse derived cells, SCT-1, β-TC cells, Hep-G2 cells, AT-T20 cells, beta-cell lines such as NIT cells or RIN cells, Ntera-2 cells (Pleasure et al., *Journ. Neuroscience*, 12, pp. 1802–15 (1992)) and human astrocyte cell lines such as U-373 and U-937.

Primary cells that may be used include, bFGF-responsive neural stem/progenitor cells derived from the CNS of mammals (Richards et al., PNAS 89, pp. 8591–8595 (1992); Ray et al., PNAS 90, pp. 3602–3606 (1993)), primary fibroblasts, Schwann cells (WO 92/03536), astrocytes, oligodendrocytes and their precursors, myoblasts, and adrenal chromaffin cells. For example, one such myoblast cell line is the $C_2C_{12}$ cell line.

Cells can also be chosen depending on the particular method of growth control and differentiation to be used. For example, stem cells can easily be used with the methods which induce differentiation by introducing a chemical substance. Generally, stem cells are undifferentiated cells which in vivo are normally quiescent but are capable of proliferation and capable of giving rise to more stem cells having the ability to generate a large number of progenitor cells that can in turn give rise to differentiated or differentiatable daughter cells. Stem cells represent a class of cells which may readily be expanded in culture, and whose progeny may be terminally differentiated by the administration of a specific growth factor. See, e.g., Weiss et al. (PCT/CA 92/00283).

Myoblasts are one type of cell that may be encapsulated in a BAO according to this invention.

Myoblasts are muscle precursor cells originally derived from mesodermal stem cell populations. A number of myoblast cell lines are available which can undergo differentiation in culture, e.g., L-6 and β-CH3 cells. Primary myoblasts can be readily isolated from tissue taken from an autopsy or a biopsy, and can be purified and expanded. Myoblasts proliferate and fuse together 35 to form differentiated, multi-nucleated myotubes. Myotubes no longer divide, but continue to produce muscle proteins. While proliferating, myoblasts may readily be genetically engineered to produce therapeutic molecules. Methods are known for introducing one or more genes into myoblasts to produce the desired biologically active molecules. Myoblasts are capable of migrating, fusing into pre-existing fibers, and serving as carriers for the introduced gene(s). Verma et al. (WO 94/01129); Blau, et al., TIG, 9, pp. 269–74 (1993); WO 93/03768; WO 90/15863. The engineered cells may then be encapsulated and allowed to differentiate in the BAO or the differentiated cells may themselves be encapsulated.

The choice of cells also depends upon the intended application. The cells within the BAO may be chosen for secretion of a neurotransmitter. Such neurotransmitters include dopamine, gamma aminobutyric acid (GABA), serotonin, acetylcholine, noradrenaline, epinephrine, glutamic acid, and other peptide neuro-transmitters. Cells can also be employed which synthesize and secrete agonists, analogs, derivatives or fragments of neurotransmitters which are active, including, for example, cells which secrete bromocriptine, a dopamine agonist, and cells which secrete L-dopa, a dopamine precursor.

The cells can be chosen for their secretion of hormones, cytokines, growth factors, trophic factors, angiogenesis factors, antibodies, blood coagulation factors, lymphokines, enzymes, and other therapeutic agents or agonists, precursors, active analogs, or active fragments thereof. These include enkephalins, catecholamines, endorphins, dynorphin, insulin, factor VIII, erythropoietin, Substance P, nerve growth factor (NGF), Glial cell line-derived Neurotrophic Factor (GDNF), platelet-derived growth factor (PDGF), epidermal growth factor (EGF), brain-derived neurotrophic factor (BDNF), neurotrophin-3 (NT-3), neurotrophin-4/5, CDF/LIF, bFGF, aFGF, an array of other fibroblast growth factors, ciliary neurotrophic factor (CNTF), and interleukins.

It should be understood from the foregoing that the cells useful in the methods of this invention include untransformed cells that secrete the desired biologically active molecule(s), or cells that can be transformed to do so.

The genes encoding numerous biologically active molecules have been cloned and their nucleotide sequences published. Many of those genes are publicly available from depositories such as the American Type Culture Collection (ATCC) or various commercial sources. Genes encoding the biologically active molecules useful in this invention that are not publicly available may be obtained using standard recombinant DNA methods such as PCR amplification, genomic and cDNA library screening with oligonucleotide probes from any published sequences. Any of the known genes coding for biologically active molecules may be employed in the methods of this invention. See, e.g., U.S. Pat. No. 5,049,493; Gage et al., U.S. Pat. No. 5,082,670; and U.S. Pat. No. 5,167,762.

A gene of interest (i.e., a gene that encodes a suitable biologically active molecule) can be inserted into a cloning site of a suitable expression vector by using standard techniques. These techniques are well known to those skilled in the art.

The expression vector containing the gene of interest may then be used to transfect the cell line to be used in the methods of this invention. Standard transfection techniques such as calcium phosphate co-precipitation, DEAE-dextran transfection, lipid-mediated methods, or electroporation may be utilized.

Methods are provided herein to control the growth of dividing cells, whereby the balance between proliferation and differentiation can be controlled to provide a supply of differentiated, non-dividing encapsulated cells within the BAO. Methods are also provided to control the growth of both dividing and non-dividing cells, whereby cell distribution and cell number within the BAO are controlled, resulting in reduced formation of necrotic cell cores and reduced cellular debris.

Control of Proliferation and Differentiation by Genetic Engineering

Methods and compositions are herein provided for controlling cell growth by genetic alteration of cells with a gene encoding a product that influences cell proliferation or differentiation.

According to one aspect of this invention, conditionally immortalized cell lines are used to achieve growth control in the BAO. Primary cells are transformed with a gene encoding a proliferation-promoting product. The proliferation-promoting gene is operatively linked to a regulatable promoter. The techniques described by Land et al., Nature, 304, pp. 596–602 (1983) or Cepko, Neuron, 1, pp. 345–53 (1988) for producing immortalized cells can be routinely modified to produce conditionally-immortalized cells.

According to this method, cell proliferation (i.e., mitosis) can be inhibited or arrested by decreased expression of a proliferation-promoting gene, such as an oncogene (e.g., c-myc, v-mos, v-Ha-ras, SV40 T-antigen, E1-A from adenoviruses). Reduced expression of the oncogene is achieved by downregulation, repression or inactivation of the promoter driving oncogene expression when the BAO is implanted in vivo in a host. Upregulation, activation or derepression of the regulatable promoter in vitro results in expression of the proliferation-promoting gene, thereby permitting cell proliferation in vitro. Suitable promoters are those which can be downregulated in vivo, including, e.g., glucocorticoid responsive promoters, such as PNMT (Hammang et al., Neuroprotocols, 3, pp. 176–83 (1993) and interferon ("IFN")-responsive promoters, such as Mx1 (Hug et al., Mol. Cell. Biol., 8, pp. 3065–79 (1988); Arnheiter et al., Cell, 52, pp. 51–61 (1990)), retroviral long terminal repeat promoters, tetracycline responsive promoters, e.g., the lac promoter, and insulin-responsive promoters. See also, McDonnell et al. WO 93/23431. It will be appreciated that choice of promoter will depend upon the intended implantation site. Thus, e.g., glucocorticoid or IFN-responsive promoters are useful for implantation in the brain according to this method, since the levels of glucocorticoid and/or IFN are very low in the brain. Thus, these promoters would not be expected to direct significant levels of expression of the oncogene upon implantation of the BAO in the brain.

In one embodiment, conditionally-immortalized cells are generated by operatively linking an oncogene to a regulatable promoter. The promoter is activated or upregulated in the presence of a binding protein. Production of the binding protein can be regulated by operatively linking the gene encoding the binding protein to a tetracycline responsive promoter.

For example, one embodiment contemplates a transformed cell containing a constitutive promoter driving tet repressor expression. The cell additionally contains a heterologous gene operatively linked to the CMV-IE promoter. If the CMV-IE promoter is flanked with tet operator sequences, expression from this promoter can be turned off by the tet repressor. In the presence of tet, transcription occurs because tet binds with the tet repressor allowing other transcription factors to bind the CMV-IE promoter. According to this embodiment, the oncogene is only expressed when tetracycline is present. Thus, cells can be proliferated in vitro in the presence of tetracycline.

Several days prior to implantation, tetracycline can be removed to reduce transgene expression, and thus correspondingly reduce or halt cell proliferation in the BAO.

In a specific embodiment using conditionally immortalized cells, growth control is achieved using the Mx1 promoter. The Mx1 gene encodes a protein which confers resistance to influenza A and B. The Mx1 gene is tightly regulated by its promoter. In the absence of interferon ("IFN"), the gene is not expressed and the gene is inducible in the presence of IFNα and IFNβ. Arnheiter et al., Cell, 52, pp. 51–61 (1990) reported the generation of Mx1 transgenic mice that exhibited interferon inducible expression of the transgene in several tissues. The SV40 large T-antigen is capable of transforming and immortalizing cells derived from a number of tissues.

In one embodiment, the mouse Mx1 promoter can be fused with the SV40 early region and the chimeric gene used to generate transgenic mice. The tight regulation afforded by the Mx1 promoter elements allows one to control oncogene expression in tissues or in cell cultures prepared from the transgenic animals, thereby allowing creation of conditionally-immortalized cell lines.

In the presence of IFNα or IFNβ, the cell lines produced in this manner can be expanded arithmetically as with most other cell lines. Cell division can be halted by removal of IFNα or IFNβ, either before or after encapsulation. In a preferred embodiment, neural stem cells (neurospheres) can be prepared from transgenic mice containing the Mx1-SV40 T-antigen construct using the method of Weiss (PCT/CA 92/00283). The conditionally immortalized neural stem cell line so obtained can then be encapsulated and implanted in vivo in a host.

Additionally, if desired, the conditionally immortalized neural stem cell line can be further genetically modified to release any of a number of growth factors or neurotransmitter molecules, according to standard techniques. Other IFN-responsive promoters may also be useful in this embodiment. These promoters include metallothionein, H-2K$^b$, H-2D$^d$, H-2L$^d$, HLA-A3, HLA-DRα, an HLA class I gene, 202, 56K, 6-16, IP-10, ISG15, ISG54, and 2',5'-oligo (A) synthetase. See, Hug et al., *Mol. Cell. Biol.,* 8, pp. 3065–79 (1988).

This embodiment is particularly suited for cells to be encapsulated in BAOs for implantation in the brain. Circulating levels of IFNα and IFNβ in the brain are sufficiently low that transcriptional activity driven by the Mx1 promoter is insufficient to result in cell proliferation. In the founder transgenic animals, the expression of T-antigen could be induced in several tissues, but the natural expression of the oncogene was seen only in the thymus. However, thymic expression of the oncogene is a relatively common phenomenon in transgenic animals expressing the SV40 early region. Thus, in the absence of significant oncogene expression, the cells can be kept in a near quiescent state in vivo.

Another embodiment makes use of the observation that in traditional retroviral infection techniques to genetically engineer cells for use in vivo, retroviral promoters, e.g., the long terminal repeat ("LTR") promoter, are used. See, e.g., Gage et al. (U.S. Pat. No. 5,082,670). The expression of genes driven by these promoters is typically downregulated in vivo. It is thought that this downregulation is mediated by circulating cytokines. This invention makes use of this normally detrimental downregulation of retroviral genes to stop or decrease cellular proliferation when cells are encapsulated within the BAO and implanted in vivo. In this instance, an immortalizing gene (oncogene) is driven from the LTR. This gene will "immortalize" the cells while they are maintained and expanded in vitro. Following implantation, in the presence of cytokines, the "immortalizing" oncogene is downregulated, proliferation decreases or stops and the cells may become quiescent within the device.

According to this embodiment conditionally-immortalized cells may be produced by retroviral infection or DNA transfection with cDNA containing an oncogene (e.g. c-myc, v-mos, v-Ha-ras, SV40 T-antigen, E1-A from adenoviruses) operatively linked to a retroviral promoter, e.g., the LTR promoter. We prefer Moloney murine leukemia virus (MLV), Rous sarcoma virus (RSV), and mouse mammary tumor virus (MMTV) promoter sequences.

These transformed cells will normally express the oncogene in vitro. Successfully transformed cells will be grown in culture using established culture techniques. LTR-transgene expression can be stimulated by the addition of dexamethasone or epidermal growth factor to shorten the amount of time needed to culture the transformed cells. By exposing the cells to cytokines, e.g., gamma-interferon (IFN-γ), TNF-α and transforming growth factor-β (TGFβ), preferably several days prior to encapsulation and implantation, mitosis can be reduced by hindering LTR-driven transgene expression. Schinstine and Gage, *Molecular and Cellular Approaches to the Treatment of Neurological Disease,* 71, ed. Waxman, S. G. (1993); Seliger et al., *J. Immunol.,* 141, pp. 2138–44 (1988); Seliger et al., *J. Virology,* 61, pp. 2567–72 (1987); Seliger et al., *J. Virology,* 62, pp. 619–21 (1988).

Any suitable cell can be conditionally immortalized according to the above methods. One of ordinary skill in the art can determine the suitability of a given cell type for conditional immmortalization by screening methods well known in the art, including according to the methods provided herein.

Methods are provided herein for growth control of immortalized cell lines or other continuously proliferating cells by transforming these cells to include tumor suppressor genes, e.g., the p53 gene or RB gene, to halt or reduce proliferation. Tumor suppressor genes, or anti-oncogenes, are believed to be growth-constraining genes. See, e.g., Weinberg, *Neuron,* 11, pp. 191–96 (1993). For example, a wild-type p53-activated fragment 1 (WAF1) can suppress tumor cell growth in culture. It is theorized that genes induced by the p53 protein may mediate its biological role as a tumor suppressor. El-Deiry et al., "WAF1, a Potential Mediator of p53 Tumor Suppression," *Cell,* 75, pp. 817–825 (1993). The WAF1 gene is also referred to as the CIP1 gene. Other p53-mediated growth arresting genes include GADD45 and GADD153 (or CHOP). See Ron *Proc. Natl. Acad. Sci. USA,* 91, pp. 1985–86 (1994). The standard techniques for transforming cells with heterologous DNA discussed above can be used here.

According to one embodiment, immortalized cells or continuously proliferating cells are transformed with a tumor suppressor gene operatively linked to a regulatable promoter. Use of a suitable regulatable or inducible promoter allows expression of the transgene to be downregulated or "turned off" when the transformed cells are cultured in vitro, thus permitting expansion. Upon encapsulation and implantation, the promoter is "induced," or upregulated, and expression of the tumor suppressor gene occurs, resulting in reduced or halted cell proliferation.

The tyrosine hydroxylase and erythropoeitin promoters may be useful in this aspect of the invention. These promoters are typically "downregulated" under high $O_2$ conditions, such as those encountered in vitro, but are "upregulated" under low $O_2$ conditions, like those that cells encounter upon encapsulation in a BAO and implantation in a host.

In addition, suitable coupled or derepressible promoter systems may be used to achieve the desired regulation of the proliferation-suppressing gene. One suitable system, e.g., involves use of the AP1 promoter and the lac operator/PGK1 promoter system described by Hannan et al., *Gene,* 130, pp. 233–39 (1993). The AP1 promoter is operatively linked to the lac repressor gene. The lacO (lac operator) and 3-phosphoglycerate kinase (PGK1) promoter is operatively linked to the proliferation-suppressing gene. Addition of exogenous phorbol ester in vitro induces the AP1 promoter, resulting in expression of the lac repressor protein. In the presence of repressor protein, the lacO-PGK1 promoter construct is repressed, and no expression of the proliferation-suppressing gene occurs. In the absence of phorbol ester in vivo, no repressor protein is expressed, the lacO-PGK1 promoter is derepressed, and the proliferation-suppressing gene is expressed.

According to one method, a suitable cell is transformed with a gene encoding a differentiation-inducing product. This differentiation-inducing gene is operatively linked to a regulatable promoter. According to this method, the differentiation-inducing gene would be expressed upon encapsulation and in vivo implantation in a host. However, expression can be arrested or inhibited in vitro by appropriate downregulation, repression or inactivation of the regulatable promoter, thus allowing expansion of a desired cell or cell line in vitro. This method can be used with dividing cells, or primary cells that have been immortalized. High mobility group chromosomal protein 14, "HMG," is one example of a gene involved in regulating differentiation of cells. Any suitable promoter that is upregulated in vivo but which can be "turned off" or downregulated in vitro can be used in this embodiment, as discussed supra for use with proliferation-arresting genes. In addition, any suitable derepressible promoter system can be used, as discussed supra, for the regulation of tumor suppressor gene expression.

Another method of growth control uses antisense RNA or DNA, or their derivatives. Antisense RNA or DNA is a single-stranded nucleic acid which is complementary to the coding strand of a gene or to the "coding" mRNA produced from transcription of that gene. If the antisense RNA is present in the cell at the same time as the MRNA, the antisense RNA hybridizes to the 35 mRNA forming a double strand which then cannot be translated by ribosomes to make protein. Antisense RNA can be administered to cells either via microinjection or bulk addition to culture medium. The preferred method of the instant invention is to transfect target cells with eukaryotic expression vectors. Neckers et al., "Antisense Technology: Biological Utility And Practical Considerations", *Am. J. Physiol.,* 265 (*Lung Cell. Mol. Physiol.,* 9), pp. L1–L12 (1993).

According to this embodiment, an antisense gene encoding antisense RNA to either a proliferation-inducing gene or a tumor suppressor gene can be operatively linked to an inducible promoter. When the promoter is induced, antisense RNA is produced. If the transformed cells contain a proliferation-inducing gene, according to this embodiment, antisense RNA production would be halted or downregulated in vitro to allow for cell expansion, and upregulated in vivo, to achieve cessation or reduction of proliferation.

Alternatively, if the transformed cells contain a tumor suppressor gene, antisense RNA production would be upregulated in vitro and downregulated in vivo to achieve the desired growth control.

In addition, antisense technology could be used to construct any antisense gene to a gene encoding a product essential for proliferation or differentiation. Appropriate induction of the expression of the antisense gene would allow one of skill in the art to achieve the desired growth control of encapsulated cells according to this invention.

It is preferred to use a regulatable promoter/gene construct that can be manipulated in vivo in the event that it becomes necessary or desirable to induce further cell proliferation in vivo. For example, in the Mx1/SV40 construct discussed supra, IFN can be added locally or systemically to induce oncogene expression. An increase in cell division in vivo in the BAO may be desirable to increase cell number to replace dead cells in the BAO, or to achieve increased output of the desired biologically active molecule from the BAO.

Control of Growth and Differentiation by Use of Chemical Compounds

According to another method of this invention, cells may be exposed to a treatment which inhibits proliferation or induces differentiation. In some methods, the treatment comprises providing a chemical compound or growth factor. In other methods, the treatment comprises removing a chemical compound or growth factor from the growth medium. The treatment may be before or after encapsulation in the BAO, preferably before encapsulation.

The protein or chemical compound used depends on the cell type and the desired effect. One of ordinary skill in the art could screen a given cell type for its responsiveness to a selected compound or protein, with routine techniques.

In one method, cell distribution is controlled by a treatment that comprises removing a proliferation-inducing chemical compound or growth factor from the cell growth medium. In one embodiment, growth factors, such as epidermal growth factor ("EGF"), transforming growth factor α ("TGF-α"), amphiregulin, or any other suitable agent, can be used to induce proliferation of stem or progenitor cells, including cells from embryonic sympathetic ganglia and immortalized progenitor cells, preferably neural stem cells (Weiss, PCT/CA 92/00283). This allows maintenance and expansion of a supply of neuronal precursor cells in vitro. When encapsulated in the absence of these proliferation-inducing growth factors, the neuronal precursor cells cease dividing and differentiate.

The neuronal precursor cells may be further induced to differentiate by treatment with, e.g., phorbol ester, or growth on a fixed substrate, including ionically charged surfaces such as poly-L-lysine and poly-L-ornithine and the like. Differentiation may also be induced by treatment with a member of the FGF family in combination with at least 1 member of either the ciliary neurotrophic factor (CNTF) or nerve growth factor (NGF) family of factors as described in Ip et al. (WO 94/03199).

In another embodiment, a multilineage growth factor produced in the stroma, also termed "mast cell growth factor," "stem cell factor," "c-kit-ligand," or "Steel factor," can be used to induce proliferation of hematopoietic stem cells. To maintain a supply of dividing cells in vitro, hematopoietic stem cells are cultured in the presence of mast cell growth factor. To arrest or reduce proliferation, the mast cell growth factor is removed from the culture medium. This can be done before or after encapsulation, preferably before encapsulation.

Examples of other multilineage growth factors that promote proliferation include interleukin-3 and granulocyte-macrophage colony-stimulating factor. Mast cell growth factor can also affect cell growth in combination with other multilineage growth factors, or lineage specific growth factors, e.g., erythropoietin. For example, mast cell growth factor is thought to act synergistically with IL-3 in inducing proliferation and differentiation of highly enriched murine hematopoietic stem cells. Galli et al., "The Biology of Stem Cell Factor, a New Hematopoietic Growth Factor Involved in Stem Cell Regulation," *Int. J. Clin. Lab. Res.,* 23, pp. 70–77 (1993).

In another method of this invention, control of cell distribution in the BAO may be achieved by providing a chemical compound or growth factor which inhibits cell proliferation or induces differentiation. Any suitable proliferation-inhibiting or differentiation-inducing compound may be used according to this method.

It will be appreciated that different cell types may respond differently to various chemical compounds. One of ordinary skill in the art can routinely screen a particular compound to determine its effectiveness in affecting proliferation or differentiation of a given cell type.

In one embodiment, cytokines, including, e.g., transforming growth factor β1 (TGFβ1), may be used to arrest or inhibit cell proliferation or to induce cell differentiation. For example, decreased proliferation and enhanced differentiation in BHK cells can be achieved by exposure to TGFα1 and ascorbate. Similarly, TGFα1 can be used to induce differentiation in fibroblast cells and also as a growth inhibitor of keratinocytes and endothelial cells. Phillips et al., "Ascorbic Acid and Transforming Growth Factor-β1 Increase Collagen Biosynthesis via Different Mechanisms: Coordinate Regulation of Proα1(I) and Proα1(III) Collagens," *Archives of Biochemistry and Biophysics*, 295, pp. 397–403 (1992).

In another embodiment, TGFβ1, serotonin, or FGF may be used to control the growth of neuroendocrine cells. The growth of neuroendocrine cells can be regulated by their own products in an autocrine fashion. TGFα1 is an autocrine growth-inhibitory factor for human pancreatic carcinoid cells (BON), while FGF and serotonin are autocrine growth-stimulatory factors. The inhibitory effect of TGFβ1 on the growth of BON cells can be reversed by addition of serotonin. Townsend Jr. et al., "Studies of Growth Regulation in a Neuroendocrine Cell Line," *Acta Oncologica*, 32, pp. 125–130 (1993).

A variety of other chemicals may also be used according to the methods of this invention to arrest or inhibit proliferation or induce differentiation of cells. These chemicals include mitomycin C, 5-bromo-deoxyuridine (BrdU), prostaglandin $E_1$ ($PGE_1$), dibutyryl cAMP, 1-β-D-arabinofuranosyl cytosine (Ara-C), nicotinamide, and heparin. Mitomycin may be particularly suited for controlling proliferation of encapsulated βHC cell lines. See, e.g., Radvanyi et al., *Mol. Cell. Biol.*, 13, pp. 4223–27 (1993).

Sometimes a combination of chemicals can be used. Human neuroblastoma cells IMR-32 may be induced to differentiate in vitro when treated with mitomycin C and BrdU or $PGE_1$ and dibutyryl cAMP (dbcAMP). Gash et al., "Amitotic Neuroblastoma Cells Used for Neural Implants in Monkeys," *Science*, 233, pp. 1420–22 (1986). Serial pretreatments of human embryonal rhabdomyosarcoma cell line with Ara-C results in marked growth inhibition in vitro, loss of tumorigenicity in vivo, and a more differentiated phenotype even following removal of the compound. Crouch et al., "Ara-C Treatment Leads to Differentiation and Reverses the Transformed Phenotype in a Human Rhabdomyosarcoma Cell Line," *Experimental Cell Research*, 204, pp. 210–16 (1993). Nicotinamide (NIC) is thought to induce differentiation and maturation of human fetal pancreatic islet cells. Otonkoski et al., "Nicotinamide Is a Potent Inducer of Endocrine Differentiation in Cultured Human Fetal Pancreatic Cells," *J. Clin. Invest.*, 92, pp. 1459–66 (1993).

The addition of dbcAMP has also been reported to influence the differentiation of developing tissues. For example, dbcAMP is thought to modulate the differentiation of astrocyte precursors, induce neurite formation in PC12 cells, and stimulate Schwann cell proliferation. Baron-Van Evercooren et al., "Schwann Cell Differentiation in vitro: Extracellular Matrix Deposition and Interaction," *Dev. Neurosci.*, 8, pp. 182–96 (1986). Similarly, differentiation of Schwann cells can be induced by exposure to ascorbate. *Ibid.*

Further, sialoglycopeptide ("SGP") molecules may be used to inhibit or arrest cell proliferation.

For example, an 18 kDa cell surface sialoglycopeptide isolated from intact bovine cerebral cortex cells arrested proliferation of exponentially growing Swiss 3T3 cells. See, e.g., Toole-Simms et al., *Jour. Cell. Physiol.*, 147, pp. 292–97 (1991); Fattaey et al., *Exp. Cell. Res.*, 194, pp. 62–68 (1991). Numerous transformed and untransformed cell types have been shown to be sensitive to some SGPS. These cells include epithelial-like and fibroblast cells from a broad spectrum of vertebrate and invertebrate species. See, e.g., Fattaey et al., *Jour. Cell. Physiol.*, 139, pp. 269–74 (1989) incorporated herein by reference.

It will be appreciated that some of the foregoing treatments may only have a transient effect on proliferation and differentiation. In such cases it may be desireable to provide a continuously replenished supply of the compound or growth factor to the encapsulated cell when implanted in vivo in the host. This can be accomplished by use of a bioerodable polymer non-cellular source of the growth factor or compound, or by co-encapsulating a cellular source of the growth factor or compound, or any other suitable means. See, e.g., U.S. Pat. Nos. 5,106,627 and 5,156,844.

Control of Growth By Irradiation

Cell proliferation can also be controlled through exposure of cells to a suitable dose of irradiation, e.g., x-rays, ultraviolet (UV) radiation, and the like. When cells are subjected to irradiation, their progression through the cell cycle may be arrested. The critical dose rate, or minimum dose rate can be determined for a chosen cell type using methods known in the art. See, e.g., Stanley and Lee, *Radiat. Res.*, 133, pp. 163–9 (1993); Mitchell et al., *Radiat. Res.*, 79, pp. 537–51 (1979). For example, normal human epidermal keratinocytes irradiated with 5 and 10 $mJ/cm^2$ ultraviolet B(UVB) radiation showed a significant (up to 78%) decrease in proliferation 3 to 5 days post-irradiation. Prystowsky et al., *J. Invest. Dermatol.*, 101, pp. 54–58 (1993). Yi et al., *Radiation Research*, 133, pp. 163–69 (1993) provide a method for calculating the lowest dosage required to stop cell proliferation by exposure to x-rays.

Control of Growth and Differentiation By Use of Extracellular Matrix Molecules

Methods are provided herein for the control of cell distribution in a BAO by modification of a growth surface with a growth controlling extracellular matrix ("ECM") (or components thereof) alone or in combination with a growth controlling physical matrix or other growth regulating substances.

In living tissue, the ECM is formed from a variety of proteins and polysaccharides which are secreted by cells and assembled into a network in proximity to the cells that secreted them. ECM molecules include glycosaminoglycans and proteoglycans, such as chrondroitin sulfate, fibronectin, heparin sulfate, hyaluron, dermatan sulfate, keratin sulfate, laminin, collagen, heparan sulfate proteoglycan (HSPG) and elastin. In particular, collagen is a major component of ECM in vivo. ECM molecules are known to cause decreased cell proliferation and increased cell differentiation. In addition, acellular ECM when used in the methods of this invention may influence the spatial location of cells encapsulated in the BAO.

ECM may be obtained by culturing cells known to deposit ECM, including cells of mesenchymal or astrocyte origin. Schwann cells can be induced to synthesize ECM when treated with ascorbate and cAMP. These ECM components resemble a precursor form of the basement membrane which support Schwann cell proliferation. Furthermore, naturally produced ECM from endothelial cells and a reconstituted basement membrane gel from Engelbreth Holm-Swarm tumor cells (EHS) supports the growth and differentiation of various epithelial and endothelial cells. Baron-Van Evercooren et al., "Schwann Cell Differentiation in vitro: Extracellular Matrix Deposition and Interaction," *Dev. Neurosci.*, 8, pp. 182–96 (1986).

In one embodiment, growth control is achieved by coating a growth surface in the BAO with ECM (or its growth controlling components). We prefer seeding the growth surface in the BAO with cells that produce ECM, and culturing the cells until confluent. The cells are then treated with detergent and $NH_4OH$. The resulting BAO, with acellular ECM coated on a growth surface, is then used to encapsulate cells that produce the desired biologically active molecule.

In another embodiment, ECM is prepared substantially in the same manner in vitro, lyophilized, fragmented and mixed with cells as a suspension. The cell/ECM fragments are then co-loaded into the BAO.

Cells grown in presence of some ECM molecules show decreased proliferation and increased differentiation compared to cells grown in conventional monolayer culture. For example, adrenocortical cells, known to synthesize certain steroid hormones such as aldosterone, exhibit decreased proliferation when grown in vitro in the presence of collagen gel. Fujiyama et al., "Influence of Extracellular Matrix on the Proliferation and Differentiation of Adrenocortical Cells in Culture," *Path. Res. Pract.*, 189, pp. 12051–14 (1993).

Schwann cells may also exhibit decreased proliferation and increased differentiation when cultured in the presence of collagen.

Endocrine cells are also known to differentiate in vitro when grown on surfaces coated with a combination of type IV collagen and HSPG. Type IV collagen is necessary for cell adhesion and the HSPG induces differentiation. de Bruine et al., "Extracellular Matrix Components Induce Endocrine Differentiation In Vitro in NCI-H716 Cells," *American Journal of Pathology*, 142, pp. 773–782 (1993).

Various growth factors or chemical compounds, including those discussed supra, may be added to the ECM components to further control the growth and differentiation of cells. Growth factors may be administered to the cells in vitro prior to implantation or to the cells in vivo, or both. See, e.g., U.S. Pat. Nos. 5,156,844 and 5,106,627, which refer to methods for delivering growth factors 35 using either a co-encapsulated cellular or non-cellular source of the growth factor. In addition, the ECM molecules may be derivatized with growth controlling peptides according to known techniques.

For example, transforming growth factor-β, which modulates cell growth on its own, and which reversibly binds to certain ECM molecules (e.g. decorin), can be added to ECM to potentiate the growth-inhibiting effects of ECM molecules.

Likewise, heparin has also been shown to prevent the growth of both untransformed cells and transformed cell lines. Matuoka et al., *Cell Structure and Function*, 9, p. 357 (1984).

Basic fibroblast growth factor (bFGF) has also been reported to enhance endocrine cell differentiation when added along with ECM components. See, de Bruine et al., "Extracellular Matrix Components Induce Endocrine Differentiation In Vitro in NCI-H716 Cells," *American Journal of Pathology*, 142, pp. 773–782 (1993).

Growth factors may exhibit different effects on cells when combined with different components of ECM. For example, fibroblast growth factor (FGF) has been shown to be an effective differentiating factor and a weak mitogen for chromaffin cells grown on laminin. However, when FGF is added to chromaffin cells grown on collagen, FGF is a weak differentiation factor and a strong mitogen. This behavior has also been shown for the cyclic AMP analogue 8-(4-chlorophenylthio) cyclic AMP. Chu et al., *Neuroscience*, 95, pp. 43–54 (1994).

Table 1 is a partial list of ECM molecules growth factors and chemical compounds known to influence proliferation and differentiation in particular cell types.

TABLE 1

ECM MOLECULES, GROWTH FACTORS AND CHEMICAL COMPOUNDS INFLUENCING PROLIFERATION OR DIFFERENTATION

| Cell Type | Differentiation Inducer/ Growth Inhibitor | Proliferation Promoter |
|---|---|---|
| Schwann | ascorbate; collagen (Vitrogen ™); Cultisphers/agarose | TGF-β; dbcAMP |
| PC12 | NGF; dbcAMP; SGP | |
| Fibroblasts | TGF-β-1; Cultisphers/agarose; ascorbate; SGP | Vitrogen ™ |
| Myoblasts | collagen; ascorbate | |
| Neural stem | laminin; Peptide 2000; Cultisphers/Peptide 2000; phorbol ester; heparin; FGF and (CNTF or NGF) | EGF; bFGF; TGF-α; amphiregulin |
| Human embryonal rhabdomyosarcoma cell line | Ara-C | |
| Human fetal pancreatic islet cells | Nicotinamide (NIC) | |
| Astroblasts | dbcAMP | |
| Swiss 3T3 | SGP | |
| Adrenocortical | Collagen | |
| Endocrine | Type IV Collagen + HSPG; bFGF + ECM components | |
| Chromaffin | FGF + laminin; 8-(4-chloro-phenylthio)cyclic AMP + laminin | FGF + collagen; 8-(4-chloro-phenylthio)cyclic AMP + collagen |
| Hematopoietic stem cells | | Mast cell Growth Factor |
| BHK | TGFβ-1 + Ascorbate; ECM from E15 rat meningeal cells | |
| Keratinocytes | TGFβ-1 | |
| Endothelial cells | TGFβ-1 | |
| Neuroendocrine (human pancreatic caranoid cells (BON)) | TGFβ-1 | TGFβ-1 + Ascorbate; Serotonin; FGF |
| Human neuroblastoma Cell line IMR-32 | Mitomycin C + BrdU; $PGE_1$ + dbcAMP; SGP | |
| SCT-1 | Collagen; Ascorbate | |

The growth surfaces within the BAO include the luminal surfaces of the BAO, and additionally include other growth surfaces, such as an inner support, that may be encapsulated within the BAO.

Microcarriers may provide a surface for cell growth. Use of microcarriers can allow a greater number of cells to be encapsulated and evenly distributed within the BAO, especially for cells that become growth contact inhibited. Several types of microcarriers are commercially available, including Cytodex (Sigma, St. Louis, Mo.) dextran microcarriers, and CultiSpher™ (HyClone Labs, Logan, Utah) macroporous gelatin microcarriers and glass microcarriers. These microcarriers are often used for the culture of anchorage dependent cells. Cell lines which have been shown to grow on macroporous gelatin microcarriers include OBHK, BHK-21, L-929, CHO-K1, rCHO, MDCK, V79, F9, HeLa, and MDBK. Microcarriers may also be made of or coated with other ECM molecules (such as FACT™ collagen coated microcarriers (Solo Hill Labs, Ann Arbor, Mich.)), or acellular ECM, substantially as described above.

In one preferred embodiment cells producing the desired biologically active molecules can be seeded onto the ECM coated microcarrier surfaces and cultured on the microcarriers in vitro, prior to encapsulation and implantation. Cherksey (WO 93/14790) refers to the culturing of cells on glass or plastic microbeads and subsequent implantation of the microbeads into the brain of a recipient.

In another embodiment according to this invention, cells seeded on microcarriers may be suspended in the presence of a suitable growth-inhibiting matrix and then encapsulated in the BAO. Such matrix material (e.g., agarose or agar for fibroblasts; collagen for adrenocortical cells) physically inhibits further cell outgrowth. Such hydrogel matrices are described in, e.g., Dionne WO 92/19195, incorporated herein by reference.

According to another aspect of this invention, agarose may also be used as a substitute for ECM by derivatization with peptide sequences to affect cell attachment to the matrix. For example, agarose hydrogels may be derivatized with peptide sequences of laminin or fibronectin.

In this method, cells are suspended in 3-D matrices composed of agarose derivatized with a peptide sequence that recognizes a cell surface receptor molecule involved in cell adhesion. Several peptide sequences have been shown (in 2-D) to promote cell adhesion. See, e.g., Pierschbacher et al., *Science*, 309, pp. 30–33 (1984); Graf et al., *Biochemistry*, 26, pp. 6896–900 (1987); Smallheiser et al., *Dev. Brain Res.*, 12, pp. 136–40 (1984); Jucker et al., *J. Neurosci. Res.*, 28, pp. 507–17 (1991). The derivatized agarose matrices of this invention allow presentation 20 of the appropriate molecular cues for cell adhesion in 3-D. The agarose concentration is preferably 1.25% w/v or less, most preferably about 1.0%. We prefer RGD-containing sequences (i.e. ArgGlyAsp; $AA_2$–$AA_4$ of SEQ ID NO:2), YIGSR-containing sequences (TyrIleGlySerArg; $AA_5$–$AA_9$ of SEQ ID NO:1), IKVAV-containing sequences (IleLysValAlaVal; $AA_{11}$–$AA_{15}$ of SEQ ID NO:3), and the like. Derivatization can be achieved using a bi-functional coupling agent, such as 1'1, carbonyldiimidazole or any other suitable method.

One particular advantage of using agarose instead of ECM components is that naturally occurring ECM components may be enzymatically degraded over time in vivo while agarose is not as readily degraded. The use of agarose is also advantageous because it is a defined product unlike materials like Matrigel®, which is derived from a tumor cell line and therefore an undefined mixture. Specifically, it has been shown that Matrigel® contains bFGF, a potent mitogen for many cell types. Agarose is a clear, thermoreversible hydrogel made of polysaccharides. In addition to physically restricting cell outgrowth, agarose itself may inhibit proliferation and induce differentiation. See, e.g., Aulthouse, in "Expression of the Human Chondrocyte Phenotype In Vitro," *In Vitro Cellular & Developmental Biology*, 25, pp. 659–668 (1989).

Agarose can be chemically modified by derivatives, e.g., PEO-PDMS, to further inhibit cell outgrowth, preferably without toxic effects to the cells.

It will be appreciated that different cell types may exhibit different responsiveness to a given ECM molecule, or to acellular ECM from a particular source. See, e.g., End and Engel, "Multidomain Proteins Of The Extracellular Matrix And Cellular Growth", pp. 79–129, in *Receptors For Extracellular Matrix*, [Eds] McDonald and Mecham, Academic Pree, New York (1991), herein incorporated by reference. One of ordinary skill can readily screen a cell type to determine its responsiveness to an ECM molecule or to acellular ECM from a specific source, to determine its effectiveness in controlling cell distribution.

Growth Control by Growth Surface Modification in the BAO

Methods are provided herein for cell growth control in a BAO by chemically modifying growth surfaces to control cell number and cell location within the BAO. Growth surfaces within the bioartificial organ can be modified to control cell attachment to the growth surface. The growth surface within the BAO can be the luminal surface of the BAO, or an internal membrane, microcarrier or inner support placed inside the BAO. With the microcarrier and inner support embodiments, cells can be cultured on these structures in vitro and subsequently encapsulated in the BAO for implantation.

The BAO membrane may be modified by a number of different known methods, including chemical modification, to produce carboxylic acid groups, amine groups, or hydroxyl groups or other reactive functional groups, or it can be modified by absorption. These reactive functional groups, otherwise not present on the polymer backbone, can subsequently be used as sites for further derivatization.

In one embodiment, the luminal surface of the BAO is modified to promote cellular attachment thereto. Controlled cell attachment to the luminal surface may be useful in enhancing cell survival. By attaching the cells preferentially to the membrane, an even distribution of cells inside the capsule can be achieved with fewer cells than that are used in immobilization techniques using a hydrogel suspension. The use of fewer cells results in a lesser amount of cellular debris. Another benefit is the enhanced diffusion of nutrients to the cells because the cells are in close contact with the membrane. If the membrane modification is used without a matrix material within the capsule, complications of transport through the gel and adsorption of proteins or cell products to the matrix material can also be avoided. Cellular attachment may be promoted by treatment of the BAO luminal surface with poly(d-lysine) of various molecular weights. The poly(d-lysine) can be adsorbed onto the BAO luminal surface from a pH 11 buffered solution. We prefer poly(d-lysine) of about 67,000 g/mole.

In addition, peptide derivatives, e.g., RGD containing sequences (ArgGlyAsp; $AA_2$–$AA_4$ of SEQ ID NO:2), YIGSR-containing sequences (TyrIleGlySerArg; $AA_5$–$AA_9$ of SEQ ID NO:1), including CDPGYIGSR (CysAspProGlyTyrIleGlySerArg; SEQ ID NO:1), as well as IKVAV containing sequences (IleLysValAlaVal; $AA_{11}$–$AA_{15}$ of SEQ ID NO:3) (preferably CysSerArgAlaArgLysGlnAlaAla SerIleLysValAlaValSerAlaAspArg (SEQ ID NO:3)), have been found to be particularly useful in promoting cellular attachment. For example, RGD (ArgGlyAsp; $AA_2$–$AA_4$ of SEQ ID NO:2), the most common of these peptides can be chemically attached to the BAO membrane, using known techniques. Some RGD (ArgGlyAsp; $AA_2$–$AA_4$ of SEQ ID NO:2) containing molecules are commercially available—e.g., PepTite-2000™ (Telios).

In another embodiment, the BAO membrane can be modified to inhibit cell attachment through adsorption of, e.g., PEO-PDMS or poly(d-lysine)-alginate. We prefer PEO-PDMS modification, particularly if the growth surface is porous. This is because PEO-PDMS will tend to diffuse through the pores and adsorb to the surface as it passes through the pores through hydrophobic-hydrophobic bonding. In particular, low molecular weight (600–3000 g/mole) PEO-PDMS is preferred.

This embodiment is particularly useful when cells are grown on microcarriers and encapsulated in the BAO. In this manner, an even cell distribution may be achieved, cell number may be controlled, and cell adhesion may be limited to the microcarrier.

In addition, compounds promoting and inhibiting cell attachment can be used in combination. For example, the luminal surface of the BAO can be treated with compounds inhibiting cell attachment, and cell-carrying microspheres, or the matrix surrounding the cells (if used), may be treated with compounds promotimg cell attachment.

In another embodiment, the interior of the BAO may be altered by providing an inert scaffold within the BAO prior to loading cells. This scaffold provides a structure for adhering and evenly distributing cells within the capsule. Compounds useful in the preparation of an inert scaffold include, poly(hydroxyethyl methacrylate) ("PHEMA") and poly(hydroxyethyl methacrylate-co-methyl methacrylate) ("PHEMA/MMA"). Furthermore, the scaffold may be derivatized with various chemicals or proteins, including those discussed supra, to further control growth and differentiation. According to this method, solutions of a suitable scaffold material are precipitated in the BAO for the desired scaffold.

Another embodiment contemplates culturing cells on a member which will serve as an internal support. The internal support may be made of any substantially biocompatible material such as titanium or a suitable polymer. The support can be in the form of a strut or may be designed to also function as a scaffold, by providing a large amount of surface area for cell growth. One example of such a scaffold material is a non-woven polyester fabric (NWPF) (Reemay, Tenn.). There are numerous types of NWPF, varying in tightness of weave and thickness of the sheet. Such technique allows precise control over number of cells in a BAO, as well as the ability to qualify the cells/scaffold prior to insertion in the BAO. Further, differentiation of cells cultured on such a material (external to the device) could be accomplished prior to insertion of the material into the device. Such a scaffold could be modified, for example, with cell adhesion peptides, to induce cellular differentiation. Additionally, the material adds strength to the BAO. The fabrication of BAOs containing an inner support is described in co-pending application Ser. No. 08/337,555, filed Nov. 10, 1994.

The BAOs useful in this invention typically have at least one semipermeable outer surface membrane or jacket surrounding a cell-containing core. The jacket permits the diffusion of nutrients, biologically active molecules and other selected products through the BAO. The BAO is biocompatible, and preferably immunoisolatory. The core contains isolated cells, either suspended in a liquid medium or immobilized within a hydrogel matrix.

It is to be understood that the foregoing methods and compositions for controlling the distribution of cells within a BAO are not exclusive. It may be desireable to use several of the methods and compositions in combination to achieve the desired growth control.

For example, it may be desirable to produce cells that have been genetically modified to include a growth controlling gene according to the methods of this invention, grow those cell on ECM microcarriers, and encapsulate the cell/microcarrier clusters in a BAO in which one or more growth surfaces have been modified to control cell distribution.

The encapsulating membrane of the BAO may be made of a material which is the same as that of the core, or it may be made of a different material. In either case, a surrounding or peripheral membrane region of the BAO which is permselective and biocompatible will be formed. The membrane may also be constructed to be immunoisolatory, if desired.

The choice of materials used to construct the BAO is determined by a number of factors and is described in detail in Dionne WO 92/19195. Briefly, various polymers and polymer blends can be used to manufacture the capsule jacket. Polymeric membranes forming the BAO and the growth surfaces therein may include polyacrylates (including acrylic copolymers), polyvinylidenes, polyvinyl chloride copolymers, polyurethanes, polystyrenes, polyamides, cellulose acetates, cellulose nitrates, polysulfones, polyphosphazenes, polyacrylonitriles, poly (acrylonitrile/covinyl chloride), as well as derivatives, copolymers and mixtures thereof.

BAOs may be formed by any suitable method known in the art. One such method involves coextrusion of a polymeric casting solution and a coagulant which can include biological tissue fragments, organelles, or suspensions of cells and/or other therapeutic agents, as described in Dionne, WO 92/19195 and U.S. Pat. Nos. 5,158,881, 5,283,187 and 5,284,761, incorporated herein by reference.

The jacket may have a single skin (Type 1, 2), or a double skin (Type 4). A single-skinned hollow fiber may be produced by quenching only one of the surfaces of the polymer solution as it is co-extruded. A double-skinned hollow fiber may be produced by quenching both surfaces of the polymer solution as it is co-extruded. Typically, a greater percentage of the outer surface of Type 1 hollow fibers is occupied by macropores compared to Type 4 hollow fibers. Type 2 hollow fibers are intermediate.

Numerous capsule configurations, such as cylindrical, disk-shaped or spherical are possible.

The jacket of the BAO will have a pore size that determines the nominal molecular weight cut off (nMWCO) of the permselective membrane. Molecules larger than the nMWCO are physically impeded from traversing the membrane. Nominal molecular weight cut off is defined as 90% rejection under convective conditions. In situations where it is desirable that the BAO is immunoisolatory, the membrane pore size is chosen to permit the particular factors being produced by the cells to diffuse out of the vehicle, but to exclude the entry of host immune response factors into the BAO. Typically the nMWCO ranges between 50 and 200 kD, preferably between 90 and 150 kD. The most suitable membrane composition will also minimize reactivity between host immune effector molecules known to be present at the selected implantation site, and the BAO's outer membrane components.

The core of the BAO is constructed to provide a suitable local environment for the particular cells isolated therein. The core can comprise a liquid medium sufficient to maintain cell growth. Liquid cores are particularly suitable for maintaining transformed cell lines like PC12 cells. Alternatively, the core can comprise a gel matrix. The gel matrix may be composed of hydrogel (alginate, "Vitrogen™", etc.) or extracellular matrix components. See, e.g., Dionne WO 92/19195.

Compositions that form hydrogels fall into three general classes. The first class carries a net negative charge (e.g., alginate). The second class carries a net positive charge (e.g., collagen and laminin). Examples of commercially available extracellular matrix components include Matrigel™ and Vitrogen™. The third class is net neutral in charge (e.g., highly crosslinked polyethylene oxide, or polyvinylalcohol).

Any suitable method of sealing the BAO may be used, including the employment of polymer adhesives and/or crimping, knotting and heat sealing. These sealing techniques are known in the art. In addition, any suitable "dry" sealing method can also be used. In such methods, a substantially non-porous fitting is provided through which the cell-containing solution is introduced. Subsequent to filling, the BAO is sealed. Such a method is described in copending U.S. application Ser. No. 08/490,113, filed Jun. 6, 1995, now U.S. Pat. No. 5,653,688 herein incorporated by reference.

One or more in vitro assays are preferably used to establish functionality of the BAO prior to implantation in vivo. Assays or diagnostic tests well known in the art can be used for these purposes. See, e.g., *Methods In Enzymology*, Abelson [Ed], Academic Press, 1993. For example, an ELISA (enzyme-linked immunosorbent assay), chromatographic or enzymatic assay, or bioassay specific for the secreted product can be used. If desired, secretory function of an implant can be monitored over time by collecting appropriate samples (e.g., serum) from the recipient and assaying them. If the recipient is a primate, microdialysis may be used.

The number of BAOs and BAO size should be sufficient to produce a therapeutic effect upon implantation is determined by the amount of biological activity required for the particular application. In the case of secretory cells releasing therapeutic substances, standard dosage considerations and criteria known to the art are used to determine the amount of secretory substance required. Factors to be considered are discussed in Dionne, WO 92/19195.

Implantation of the BAO is performed under sterile conditions. Generally, the BAO is implanted at a site in the host which will allow appropriate delivery of the secreted product or function to the host and of nutrients to the encapsulated cells or tissue, and will also allow access to the BAO for retrieval and/or replacement. The preferred host is a primate, most preferably a human.

A number of different implantation sites are contemplated. These implantation sites include the central nervous system, including the brain, spinal cord, and aqueous and vitreous humors of the eye. Preferred sites in the brain include the striatum, the cerebral cortex, subthalamic nuclei and nucleus Basalis of Meynert. Other preferred sites are the cerebrospinal fluid, most preferably the subarachnoid space and the lateral ventricles. This invention also contemplates implantation into the kidney subcapsular site, and intraperitoneal and subcutaneous sites, or any other therapeutically beneficial site.

In order that this invention may be better understood, the following examples are set forth. These examples are for purposes of illustration only, and are not to be construed as limiting the scope of this invention in any manner.

EXAMPLES

Example 1

Growth Control Using the Mx1 Promoter

The mouse Mx1 promoter was fused with the SV40 early region and the chimeric gene was used to generate transgenic mice. Because the Mx1 promoter elements are induced in the presence of IFNα or IFNβ, oncogene expression in tissues or in cell cultures prepared from the transgenic animals can be controlled. Thus, conditionally-immortalized cell lines can be generated.

Production Of Transgenic mice

The Mx1-Tag construct we used consisted of approximately 2 kb of the Mx1 promoter (i.e., Xba1-EcoR1 fragment) fused to an intact SV40 early region cDNA, which encodes both large T and small T antigens and is fused upstream of the mouse beta globin 3' untranslated region and poly-A signal (BamH1-Xba1 fragment). The beta globin sequences were included to provide splice sites and to enhance expression of the cDNA in transgenic animals. FIG. 1 shows the plasmid map of the Mx-1 construct.

Transgenic mice containing the Mx1-Tag construct were produced by the standard technique of pro-nuclear microinjection into single-cell fertilized mouse ova (Brinster et al., *Proc. Natl. Acad. Sci. USA*, 82, pp. 4438–4442 (1985)). Southern blot analysis of tissues from the founder animals confirmed that intact copies of the transgene were integrated in the genome.

Offspring from these mice were confirmed as "DNA positive" using PCR amplimers that recognize sequences of the SV40 early region.

Conditionally-Immortalized Stem Cells

Striata were removed from E15 transgenic mouse embryos and DNA negative littermates and plated in primary (individual) cell culture in EGF-containing neurospheres medium (per 100 mls: $DDH_2O$ 50 ml, 10 X DMEM/F12 10 ml, 30% glucose 2.0 ml, $NaHCO_3$ 1.5 ml, 1M HEPES 0.5 ml, L-glutamine 1.0, 10 X hormone mix 10 ml, $DDH_2O$ 25 ml (to wash filter)). Neurospheres were prepared according to the method of Weiss, PCT CA92/00283, and Reynolds and Weiss, *J. Neuroscience*, 12, pp. 4565–74 (1992). Cells were passaged seven times once a week and then divided into 2 groups: with and without exogenous interferon (IFN). Cells were placed in T25 flasks at a plating density of 500,000 cells/5 ml in EGF-containing neurosphere medium. 1000 units/ml IFN were added to ½ of the cells. Control neurospheres received no IFN. The cells were incubated at 37° C., 5% $CO_2$ and were passaged weekly.

After 30 passages (23 with IFN), the cells were placed in serum-containing medium (DMEM, 5% fetal bovine serum, and 1X L-glutamine) with 1000 units of IFN at a cell density of 1.25 million cells in 15 ml. Fresh IFN was added every other day.

Seven days later, the medium was removed, the cells were washed with Hanks' Balanced Salt Solution (HBSS), and the flask was lightly trypsinized. The cells were resuspended in 10 ml of the serum-containing medium, spun down at 1000 RPM for 2 minutes, and the medium was aspirated off. The cells were then resuspended in 2 ml of serum medium by triturating with a fire-polished pipet.

Approximately 25,000 cells were plated on poly-ornithine-treated coverslips in DMEM with 5% FBS. IFN was added to half of the coverslips (1000 units/ml) every other day. Cells were stained for SV40 T-antigen (Tag) and glial fibrillary acidic protein (GFAP), an intermediate filament protein specifically expressed in astrocytes, at various intervals, according to the following protocol.

Coverslips were immersed in 4% paraformaldehyde in 0.1M phosphate buffered saline (PBS) for 20 mins. at room temperature, and then washed twice for 5 mins. in PBS. Cells were permeabilized in 100% EtOH for 2 min, and then washed again twice for 5 min. in 0.1 M PBS. Cells were blocked with 5% NGS (normal goat serum) diluted in 0.1 M PBS for at least 30 mins at room temperature. Primary antibodies were pooled and diluted in 1% NGS for 2 hrs. and were applied to the coverslips at room temperature, as follows: anti-Tag (mouse monoclonal) was diluted 1:10, anti-GFAP (rabbit polyclonal) was diluted 1:500. The primary antibodies were removed and the coverslips were then washed twice for 5 mins. with PBS.

Secondary antibodies were pooled and diluted in 1% NGS and were applied to the coverslips for 30 min. at room temperature in the dark, as follows: GAM-FITC (1:128); GAR-Texas Red (diluted 1:100). The secondary antibodies were removed and the coverslips were washed twice for 5 mins. with PBS in the dark.

The coverslips were mounted with Citiflour™ (or other anti-fadent mounting media) onto slides and stored at 40° C. until viewing using a fluorescent microscope equipped with rhodamine and fluorescein optics.

In this set of experiments, we set out to determine how quickly T-antigen levels fall upon the removal of the interferon. In addition, we were interested to determine the effect of T-antigen level on cell proliferation and differentiation. Differentiation was assessed by monitoring GFAP level. GFAP is an intermediate filament protein specifically expressed in mature astrocytes. The following immunofluorescence results were observed.

|     | IFN (1000 units/ml) |      | Control (No IFN) |      |
| --- | --- | --- | --- | --- |
| Day | Tag | GFAP | Tag | GFAP |
| 1   | +++ | −    | +++ | −    |
| 4   | +++ | −    | +   | +/−  |
| 7   | +++ | −    | +/− | +/−  |
| 10  | +++ | −    | −   | +    |

Thus, as shown by Tag and GFAP immunostaining, after a period of time in the serum medium, the IFN-treated cells showed continued expression of T-antigen, continued proliferation, and no evidence of GFAP expression, while the controls (no IFN) began to differentiate (upregulated GFAP expression) and ceased dividing. This was confirmed by a visual inspection of the coverslips—there was a clear cut difference in cell numbers by day 4. By day 10, the IFN-treated cells were much more numerous than the controls.

The expression of the SV40 T-antigen in this construct is regulated in a dose-dependent manner. In the cell lines we have produced, maximal T-antigen expression (measured by immunofluorescence) was observed at an IFN dose of 500–1000 units/ml. At 100 units/ml we observed minimal to no expression. As would be expected, the rate of proliferation correlated with the IFN dose; there was little or no cell division at 100 units/ml of IFN.

In further studies with the above described Mx1 Tag EGF-responsive neural stem cells, we have shown that proliferation and differentiation can be controlled. A population of these stem cells were forced to differentiate by removing EGF and adding FBS. With the addition of 1000 Units/ml of alpha/beta IFN, clusters of flat, astrocyte-like cells began to proliferate and eventually filled the culture dishes.

We have continuously maintained these cells in IFN for over 70 passages and have maintained a doubling rate of 24–36 hours over this period. When probed with a panel of neural and glial-specific antibodies, these IF-treated cells were virtually all nestin- and T-antigen-positive but were weakly immunoreacitve for glutamine synthetase and were GFAP-negative.

Upon removal of the IFN, these flat cells rapidly decreased their rate of division, lost T-antigen immunoreactivity and gradually increased glutamine synthetase and GFAP immunoreactivity. These cells survive for several months in vitro and no proliferation is evident in the continued absence of IFN. Interestingly, T-antigen immunoreactivity and cellular proliferation can be re-induced with the addition of IFN. This provides a cell line with the capacity to proliferate or differentiate in a controlled fashion.

Example 2

Cells Prepared according to Example 1 are encapsulated and implanted in a human host.

Preparation of PAN/PVC Fibers

Permselective hollow fibers are prepared via a dry jet-wet spinning technique (Cabasso, Hollow Fiber Membranes, vol. 12, Kirk-Othmer Encyclopedia of Chemical Technology, Wiley, N.Y., 3rd Ed., pp. 492–517, 1980; Dionne, WO 92/19195; U.S. Pat. No. 5,158,881). Asymmetric hollow fibers are cast from solutions of 12.5% polyacrylonitrile polyvinyl chloride (PAN/PVC) copolymer in dimethyl sulfoxide (w/w). Single-skinned or double-skinned fibers are produced. The fibers are collected into a non-solvent water bath, glycerinated, and dried. Cells are loaded at a density of 25,000 cells/$\mu$l into a PAN/PVC single-skinned hollow fiber and sealed by heat pinching.

Implantation Into Host

The encapsulated cells are implanted into a human host. Implantation sites include the lateral ventricles and striatum of the brain. Procedures for implantation of BAOs into the brain are described in Aebischer et al., WO 93/00127, incorporated herein by reference.

Example 3

Conditional Immortalization Of Neonatal Astrocytes

A fragment containing the promoter elements of mouse mammary tumor virus (MMTV) is fused to the SV40 early region CDNA. E15 rat brain derived neonatal astrocytes are transfected by electroporation and transformants selected by assaying for proliferation. Dividing cells are removed, expanded and assayed for expression of large T-antigen, using anti-large T antibodies. Transformed cells are encapsulated in BAOs and implanted in a host, substantially as described in Example 2. The BAOs are held in vivo for one month. The BAOs are then retrieved and the cell distribution in the BAOs compared to cohorts held in vitro for the same time period.

Example 4

Collagen-Reduced Proliferation and Ascorbate-Induced Differentiation Of SCT-1 Cells SCT-1 cells were cloned from a sciatic nerve tumor from a Po-SV40 transgenic mouse (Messing et al., J. Neuroscience, 14, pp. 3533–39 (1994). These SCT-1 cells were immunoreactive for the Schwann cell markers S100 and Po, as well as for SV40 T-antigen.

SCT-1 cells were grown under three conditions: (1) on tissue culture plastic without ascorbate, (2) on tissue culture plastic in the presence of 50 $\mu$g/ml ascorbate to induce differentiation, and (3) suspended in Type I collagen.

On a plastic substratum in the absence of ascorbate, most cells displayed a fibroblast-like morphology. However, some bipolar cells were present. Cells doubled in 18–20 hours and displayed no contact inhibition.

SCT-1 cells grown in the presence of ascorbate demonstrated slower growth and a more robust staining for fibronectin and type IV collagen. Laminin immunoreactivity, on the other hand, was similar in control and ascorbate-induced differentiated cultures.

SCT-1 cells suspended in Type I collagen exhibited a bipolar morphology and a dramatic decrease in mitotic activity (i.e., doubling time was $\geq$30 days).

Example 5

Inhibition Of BHK Cell Proliferation By Ascorbate and TGF-β

BHK cells secreting CNTF were grown in DMEM (high glucose) medium. Treatment of subconfluent BHK cultures with TGF-β1 (2.5 ng/ml) and ascorbate (100 μM) reduced mitosis. In addition, the cells appeared elongated, with some cells aligning. This data indicates TGF-β1 and ascorbate inhibits proliferation and induces differentiation of BHK cells.

In further experiments, BHK cells secreting hNGF were treated with 2.5 ng/ml TGFβ and 100 μM ascorbic acid prior to encapsulation in BAOs and implantation. Non-treated cells served as controls. The specific variables include: a) TGFβ/ascorbate, no Vitrogen™, b) TGFβ/ascorbate, Vitrogen™, c) no TGFβ/ascorbate, Vitrogen™, and d) no TGFβ/ascorbate, no Vitrogen™. In addition, several different polymers were used. Capsules were implanted into the striatum of adult rats. Rats were sacrificed after 3 mos.

Example 6

Neural Stem Cells Proliferate in the Presence of EGF and Differentiate in its Absence Neurospheres were prepared using the methods of Weiss et al., PCT/CA 92/00283. Passage 68 neurospheres were collected and divided. Half of the neurospheres were triturated into a single cell suspension and half remained as clusters. A single cell count was performed on a single cell suspension and it was assumed that the clustered cells were of the same concentration. Single cells and clusters were suspended separately in equal amounts of Vitrogen™ and either neurosphere medium with 20 ng/ml EGF as controls, or PC-1 medium.

Cells were loaded at a density of 25,000 cells/μl into single-skinned hollow fiber PAN/PVC BAOs, prepared substantially as described in Example 2, and then hub sealed. The BAOs were held in either neurosphere+EGF medium or in PC-1 medium (with no EGF).

The BAOs were sacrificed after 3 days and 7 days and were stained for glial fibrillary acidic protein (GFAP) by immunocytochemistry. GFAP is an intermediate filament protein specifically expressed in astrocytes. GFAP reactivity indicates that the neural stem cells have differentiated into astrocytes. The following results were observed:

|  | Time (days) | GFAP Reactivity |
| --- | --- | --- |
| Single cell, no EGF | 3 | Small % + for GFAP |
| Single cell, EGF | 3 | Negative |
| Cell clusters, no EGF | 3 | Small % + for GFAP |
| Cell clusters, EGF | 3 | Negative |
| Single cell, no EGF | 7 | Intense + for GFAP |
| Single cell, EGF | 7 | Negative |
| Cell Clusters, no EGF | 7 | Intense + for GFAP |
| Cell Clusters, EGF | 7 | Negative |

By day 7, the encapsulated neural stem cells had differentiated into astrocytes in the absence of EGF.

Example 7

Effect of ECM on BHK Cells

Preparation of Acellular ECM

E15 rat meningeal cells obtained from 15 day old embryonic rats were plated in multiwell plates and allowed to become confluent. The cells were monolayer contracted after 2 weeks and were allowed to regrow.

Acellular ECM was extracted by treatment with 0.1% Triton X-100 detergent for 30 mins, and then treatment with 5 mM $NH_4OH$ for 3 mins.

BHRK-hNGF Cells

A BHK cell line secreting NGF was produced as follows. A 2.51 kb fragment containing approximately 37 bp of the 3' end of the first intron, the double ATG sequence believed to be the protein translation start for pre-pro-NGF and the complete coding sequence and entire 3' untranslated region of the human NGF gene (Hoyle et al., *Neuron*, 10, pp. 1019–34 (1993)) was subcloned into the DHFR-based PNUT expression vector immediately downstream from the mouse metallothionein-l promotor (−650 to +7) and the first intron of the rat insulin II gene (Baetge et al., *Proc. Natl. Acad. Sci.*, 83, pp. 5454–58 (1986)).

Baby hamster kidney (BHK) cells were transfected with the pNUT-βNGF construct using the calcium phosphate method. BHK cells were grown in DMEM containing 10% fetal bovine serum, 1 x penicillin/streptomycin/ampicillin B (0.8 g/l), and L-glutamine (GIBCO) in 5% $CO_2$ and at 37° C. Transfected BHK cells were selected in medium containing 200 μM methotrexate (Sigma) for 3–4 weeks and resistant cells were maintained as a polyclonal population either with or without 200 μM methotrexate.

The transformed BHK-hNGF cells were plated at a density of $1.0 \times 10^4$ cells/well in the plates containing extracted ECM from meningeal cells. BHK-hNGF cells were also plated at the same density in control plates not containing ECM. Cells were counted using a hemacytometer after 6 DIV.

Cell counts for the control wells averaged $4.5 \times 10^6 +/- 4.5 \times 10^5$ cells. The cell counts for the extracted ECM plates averaged $9.9 \times 10^5 +/- 4.9 \times 10^5$ cells. These results show a 4.5 fold decrease in cell growth on the treated plates.

Example 8

Adherence Of Cells To Acellular ECM On An Inner Support

In further experiments, primary menigeal cells were seeded onto a TECO™ polyurethane fiber. Such fibers are useful as inner supports in BAOs. DMEM supplemented with 10% FBS was used as the culture medium. After 2 weeks, the fibers were extracted with 0.1% Triton X-100 for 30 minutes, followed by 25 mM $NH_4OH$ for 3 mins. Some fibers were immunostained with antifibronectin antibody to confirm the presence of acellular ECM on the fiber. Other fibers were used in a cell adhesion assay with BHK cells.

Example 9

BHK Cell Growth on Microcarriers Encapsulated in BAOs Modified with PEO-PDMS Preparation of PEO-PDMS Derivatized BAOs Single-skinned PAN/PVC hollow fiber BAOs were produced as described in Example 2. These BAOs had an ID of 642.6±36.7 μm, an OD of 787.8±32.2 μm, a wall thickness of 67.8±16.2 μm, a BSA rejection coefficient of 100%, and a hydraulic permeability of approximately 21.8 ml/min/m²/mmHg.

The PAN/PVC BAOs were derivatized with PEO-PDMS under sterile conditions. A 1% or 5% (v/v) solution of PEO-PDMS (Huls, PS073, MW=3126 g/mole; 82% PEO by weight) was prepared by diluting 1 ml or 5 ml of PEO-PDMS to 100 ml with deionized water. The solution was sterile filtered (0.2 µm) prior to injection into a "wet" PAN/PVC membrane. The membrane was heat pinched and immersed in an aqueous solution. The fibers were rinsed with Hanks' Buffered Salt Solution after 72 hrs and prior to use with cells.

NGF-secreting BHK cells as described in Example 7, were loaded into the PEO-PDMS derivatized fibers as follows.

Loading and Sealing Procedure

Single cell suspensions of NGF-producing BHK cells grown to 90% confluency were rinsed with PBS (lacking calcium and magnesium), trypsinized for approximately 1 minute and pelleted by centrifugation at 1000 rpm for 3 minutes. The cells were resuspended in medium to a final cell concentration of $2 \times 10^7$ cells/ml.

Cells were either loaded directly into the PEO-PDMS derivatized fibers, or mixed with a 0.15% Vitrogens® matrix solution or 0.5% agarose solution, and then loaded. Approximately 2.5 microliters (ul) of cells or cell/matrix slurry (10,000 cells/ul) were loaded into each fiber using a 24-gauge beveled catheter tip and a Hamilton syringe.

Capsules were sealed by mounting a 1–1.1 cm length of dry hollow fiber onto a hub with a septal fixture at the proximal end which has loading access for cells to be injected into the lumen of the device. After infusing 2.5 µl of the cellular suspension, the septum was cracked off and the access port sealed using a light-cured acrylate (Luxtrak™ LCM 24, ICI Resins US, Wilmington, Mass.) ("hub" sealed). The capsules were subsequently "tethered" by placing a 1.5 cm 0.020" silastic tube over the acrylic hub.

Figure 2:
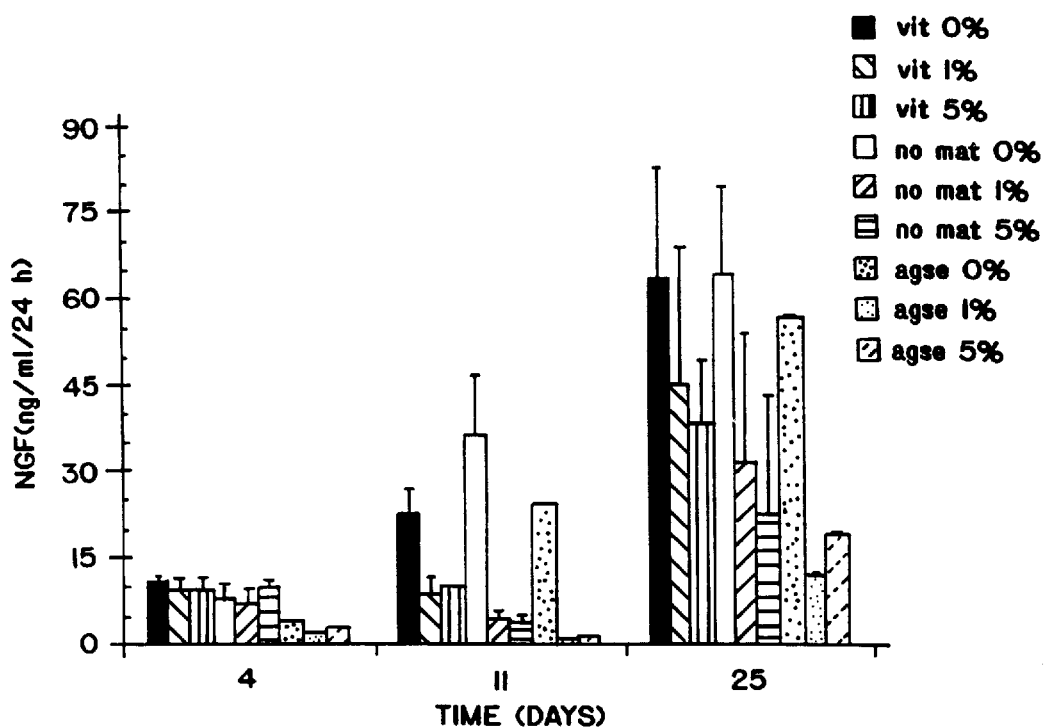
FIG. 2 shows NGF secretion (ng/ml/24 h) after 4, 11 and 25 days from BHK cells encapsulated in control, underivatized membranes (shown as "0%" in legend) or 1% or 5% PEO-PDMS derivatized membranes (shown as "1%" and "5%", respectively, in legend). Cells were encapsulated with no matrix (shown as "no mat" in legend), a Vitrogen™ matrix (shown as "vit" in legend), or an agarose matrix (shown as "agse" in legend).

The following BAOs were prepared in this manner:
1. control underivatized jacket, no matrix;
2. control underivatized jacket, Vitrogen® matrix;
3. control underivatized jacket, agarose matrix;
4. 1% PEO-PDMS derivatized jacket, no matrix;
5. 1% PEO-PDMS derivatized jacket, Vitrogen® matrix;
6. 1% PEO-PDMS derivatized jacket, agarose matrix;
7. 5% PEO-PDMS derivatized jacket, no matrix;
8. 5% PEO-PDMS derivatized jacket, Vitrogen® matrix;
9. 5% PEO-PDMS derivatized jacket, agarose matrix; The BAOs were maintained at ambient $O_2$ for 4 days after encapsulation, and then maintained at low $O_2$ levels (50 mmHg) for the duration of the study. FIG. 2 shows NGF secretion (measured by ELISA) after 4, 11 and 25 days.

The NGF release data indicates that the matrix alone has little effect on the output of the cells. However, in the presence of PEO-PDMS, the NGF release is substantially lower when used with agarose and without a matrix but not affected by when used with Vitrogen™. In addition, the percent of PEO-PDMS used in the modification apparently had little effect on NGF release. From the histology data, the BHK cells encapsulated with agarose had an elongated morphology and lined the walls of the device; however, very few cells were viable within the agarose itself. The BHK cells loaded with agarose in PEO-PDMS-modified fibers also lined the inner luminal surface of the capsule but had a round morphology. There were fewer cells in the PEO-PDMS-PAN/PVC modified fibers than there were in the unmodified fibers with agarose, indicating that cell growth was controlled. The cells in Vitrogen™ loaded devices were not affected by the fiber modification neither were those encapsulated without a matrix.

BHK cells in unmodified fibers with a Vitrogen™ matrix were well distributed with approximately 75% viability. There was some cell necrosis in the center of the device. PEO-PDMS modification did not affect cell distribution, viability or morphology. With agarose as the matrix, cell distribution was excellent with cell viability approximating 90%. The cell morphology of BHK cells was affected by PEO-PDMS derivatization of the membrane (1% and 5%) when an agarose matrix was used. The cells were elongated in unmodified P(AN/VC) and more rounded in modified P(AN/VC). Cells were not located in the agarose matrix, but in a space between the fiber and agarose "rod". Without a matrix, the cell distribution is less satisfactory as cells have formed large clusters and the viability is lower (approximately) 60%.

Example 10

BHK Cell Growth on CultiSphers™

NGF-secreting BHK cells as described in Example 7 were grown on collagen coated CultiSphers™. CultiSphers™ (1 g) were rehydrated in 50 ml of PBS (CMF). $15 \times 10^6$ cells were suspended in 1 ml of rehydrated CultiSphers™. The cell/CultiSphers™ suspension was loaded directly into single-skinned PAN/PVC hollow fibers, or mixed in a 1:1 ratio with 1% agarose, and then loaded into single-skinned PAN/PVC hollow fibers. The fibers were prepared substantially as described in Example 2, and loaded and sealed substantially as described in Example 9.

Figure 3:
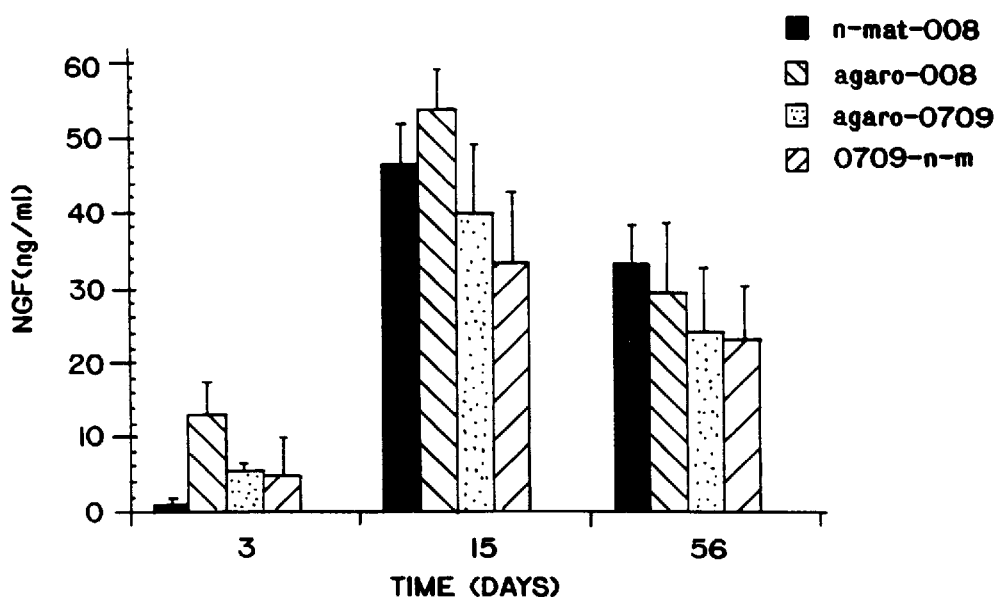
FIG. 3 shows NGF release from BHK cells grown on CultiSphers™ in the absence of an agarose matrix (legend: n-mat-008, 0709-n-m) or in the presence of an agarose matrix (legend: agaro-008, agaro-0709).

The encapsulated cells were tested for NGF secretion by ELISA at 2, 15, and 56 days. The medium was replenished 3 times/week. FIG. 3 shows the results. The NGF release data indicate that BHK cells can grow on CultiSphers™ microcarriers when encapsulated in BAOs (FIG. 3, legend: n-mat-008, 0709-n-m). Further, the NGF release data indicate that BHK cell/CultiSphers™ can be further suspended in an agarose matrix, with little or no effect on NGF secretion (FIG. 3, legend: agaro-008, agaro-0709).

Example 11

Use of a Peptide Derivative to Control Cell Number and Cell Distribution

In this example, the luminal surface of the BAO was modified with PEO-PDMS, poly(d-lysine), or PepTite 2000™, a commercially available cell adhesion protein.

In this study baby hamster kidney (BHK) cells were used because they are anchorage-dependent cells and have been shown previously to adhere to the hollow fiber membrane.

Fibers

Single-skinned PAN/PVC BAOs were produced substantially as described in Example 2. The fiber dimensions were 625 µm ID, 50 µm wall thickness.

These fibers were sterilized by immersion in 70% ethanol overnight and then rinsed repeatedly with HBSS.

Derivatization

1. PDMS-PEO: BAOs were derivatized with PDMS-PEO as follows. A 1% (v/v) solution of PEO-PDMS (purchased from Huls, PS073, Mw=3126 g/mole; 82% PEO by weight) was prepared by diluting 1 ml of PEO-PDMS to 100 ml with deionized water. The solution was sterile filtered (0.2 µm) prior to injection into a sterile 20 membrane. The membrane was immersed in a 1% PEO-PDMS aqueous solution for 24 h at room temperature. The fibers were rinsed with water (3 times) and then HBSS prior to injection of cells.

2. PdL: BAOs were derivatized with poly(d-lysine) as follows. Fibers were immersed in an aqueous solution of 67,000 molecular weight poly(d-lysine) at 2 mg/ml for 24 h at room temperature. The fibers were rinsed 3 times with water and then 3 times with HBSS prior to injection of cells.

3. PepTite 2000™: BAOs were derivatized with PepTite 2000™ as follows. Fibers were immersed in a PBS solution of 100 mg/ml of PepTite 2000™ previously dissolved in ethanol. The fibers were immersed in this solution for 24 h at room temperature and then rinsed 3 times with PBS prior to injection of cells.

4. PAN/PVC: Control fibers were immersed in HBSS for 24 h at room temperature prior to injection of cells.

Cells

BHK cells were loaded into the derivatized fibers at a concentration of 5000 cells/μl. The fibers were sealed and placed in screw-cap tubes containing serum-free medium (PC1 medium) and then placed on a rotating drum for up to two weeks in an incubator set at 37° C. The drum speed was 2 rpm. At the appropriate time the fibers were fixed in 4% paraformaldehyde, dehydrated in graded ethanol and stained with hematoxylin and eosin (H&E) for histological analysis of cell distribution with osmium tetraoxide.

PAN/PVC-derivatized membranes showed a good distribution of cells when derivatized with poly(d-lysine) and a more even distribution of cells when derivatized with PepTite™ 2000, as determined by osmium tetroxide staining.

For PAN/PVC membranes, PepTite 2000™ modifications were attempted in two ways. First, the inner luminal surface of the membranes was modified only and second, both the inner luminal surface and the outer surface were treated. Empty BAOs (i.e. free of cells) were analyzed for total amino acids, to determine the binding of poly(d-lysine) or PepTite 2000™. The total amino acid bound to control, unmodified membranes was approximately 0.2 μg/BAO. The total amino acid bound to poly(d-lysine)-modified membranes was approximately 0.8 μg/BAO for modified inner luminal surface membranes, and approximately 2.6 μg/BAO for membranes where both the inner luminal surface and outer surface had been modified. Similar BAOs loaded with BHK cells were maintained for 14 days, and then examined histologically. In control unmodified BAOS, cells were unevenly located in large clusters over the entire length of the fiber. In contrast, in both types of modified fibers, there was an even distribution of cells along the luminal surface of the membrane.

These results suggest that poly(d-lysine) and PepTite 2000™ are effective in promoting cell attachment to the BAO luminal surface, and thus are effective in controlling cell distribution within the BAO.

Example 12

Use of ECM Molecules to Control Growth of Neurosperes

Passage 71 mouse neurospheres were prepared substantially as in Example 1. Multi-well dishes were precoated with 0.5% agarose (Sea-Prep™) to keep the neurospheres from attaching to the plastic dishes. Cells were plated at a density of approximately 50,000 cells per well into the designated matrices for the experiment. Three wells were used for each matrix condition; two of the wells contained PC-1 medium (control) and one contained neurospheres +EGF medium(EGF).

A dermal-derived Type 1 collagen (Zydast™; (Collagen Biomedical, Palo Alto)), a tendon-derived Type 1 collagen (Organogenesis™), a Type 1 collagen (Vitrogen™, Celtrix, Santa Clara), and agarose were evaluated for effectiveness in controlling cell growth, alone, or in combination with laminin or PepTite 2000™, or both.

At 4 days and 14 days cells were assayed by staining with fluorescein diacetate/propidium iodide (FDA/PI), and were evaluated for cell viability, growth, and differentiation. Cells exposed to a ombination of the Organogenesis™ collagen, Peptite 2000™ and laminin showed the highest amount of differentiation, with about 90% of the cells having undergone differentiation. About 80% of cells exposed to a combination of agarose, Peptite 2000™ and laminin had differentiated.

Example 13

Use of an Inert Scaffold to Control BHK Cell Number and Cell Distribution in a BAO Two types of PAN/PVC fibers (substantially as described in Example 2) were used: a single-skinned fiber having the permselective membrane on the outer surface, and a single-skinned fiber having the permselective membrane on the inner surface.

First, PAN/PVC fibers were deglycerinized and sterilized by immersion in 70% sterile filtered ethanol overnight. The fibers were then rinsed with sterile water three times over the course of about 1 to 2 hours.

Next, a 15% concentration poly(hydroxyethyl methacrylate) ("PHEMA") scaffold matrix was prepared by dissolving 1.5 g PHEMA in 10 ml of 95% ethanol (190 proof, Quantum). In addition, a 10% concentration poly (hydroxyethyl methacrylate-co-methyl methacrylate) ("PHEMA/MMA") scaffold matrix was made by dissolving 1.0 g of PHEMA/MMA in 10 ml of 95% ethanol. To dissolve the polymers more easily, the solution was stirred and heated.

The PHEMA or PHEMA/MMA solutions were loaded with a syringe into the PAN/PVC fibers, which were then immersed in sterile water. The loaded fibers were left in water for more than 1 hour to ensure precipitation of the scaffolds and diffusion of ethanol out of the core. The ends of the fibers were cut off because they were often clogged with either PHEMA or PHEMA/MMA. The fibers were transferred to Petri dishes containing sterile HBSS. BAOs loaded with PHEMA, PHEMA/MMA and control BAOs were prepared in this manner.

NGF-secreting BHK cells (described in Example 7) were grown in 10% DMEM with glutamine and antibiotics added. The cells were gently pulled off the flasks with 0.25% trypsin, washed and resuspended in PC1 media to a density of $1 \times 10^7$ cells/ml.

The BHK-NGF cells were loaded into the fibers at a density of 10,000 cells/μl using a 22 gauge Teflon catheter. BAOs were sealed by heat pinching.

Five BAOs of each type were prepared. Four were placed in a 24 well plate with 1 ml of PC-1 media. The fifth was placed in approximately 3–4 ml of PC-1 media in a vertical tube. After 24 hours, the BAOs placed in the vertical tube were cut open along the lumen (longitudinal cross-section) and analyzed after 24 hours by staining with fluorescein diacetate/propidium iodide (FDA/PI) for cell distribution within the fibers. When viewed under a fluorescent microscope, FDA stains viable cells green and PI stains nonviable cells red.

The remaining BAOs were cultured for 2 weeks. The BAOs were maintained at ambient $O_2$ for 4 days after encapsulation, and then maintained at low $O_2$ levels (50 mmHg) for the duration of the study.

The functionality of BHK-NGF cells was tested by measuring NGF secretion (by ELISA) after 4, 7 and 14 days. The cells PHEMA or PHEMA/MMA scaffold-containing BAOs continued to secrete NGF over the duration of the study. Both the histology and NGF-release data indicate that PHEMA and PHEMA-MMA scaffolds allow maintenance of functionally-active viable cells distributed along the BAO. The results with 10% PHEMA-MMA scaffolds were the best.

Example 14

Use of an Inert Scaffold to Control PC12A Cell Number and Cell Distribution in a BAO The effectiveness of PHEMA and PHEMA/MMA inert scaffolds were evaluated for effectiveness in controlling the distribution of PC12 in BAOs.

Single-skinned fibers were prepared substantially as described in Example 2. These fibers typically had the following characteristics: 642 µm ID, 787 µm OD, wall thickness 68 µm, rejection coefficient 100% (BSA), hydraulic permeability 22 ml/min/m²/mm Hg.

Inert scaffolds of PHEMA and PHEMA/MMA were prepared in these fibers, substantially as described in Example 13.

Figure 4A:
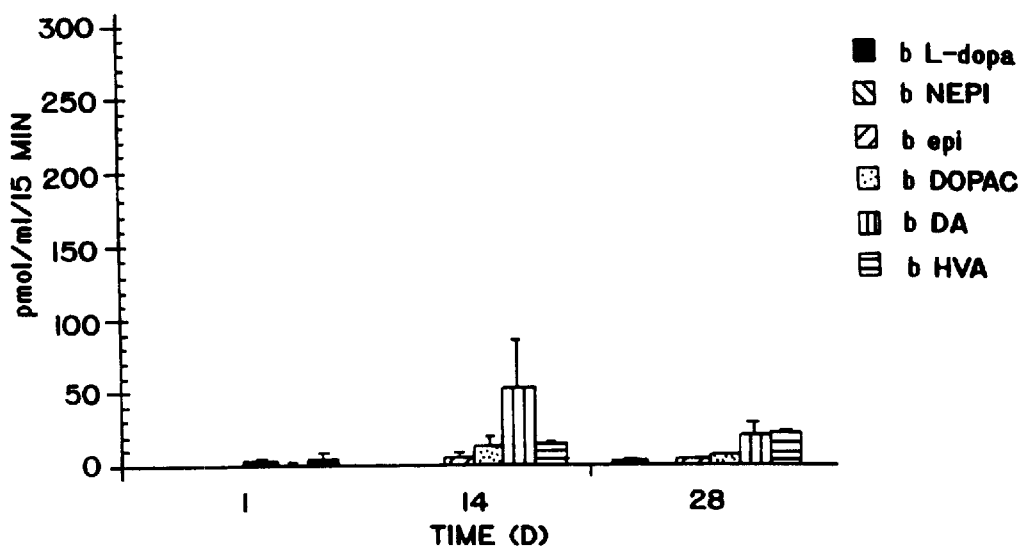
FIGS. 4A and 4B show release of catecholamines from PC12A cells at 1, 14 and 28 days after encapsulation in BAOs having a inert PHEMA scaffold.
Figure 4B:
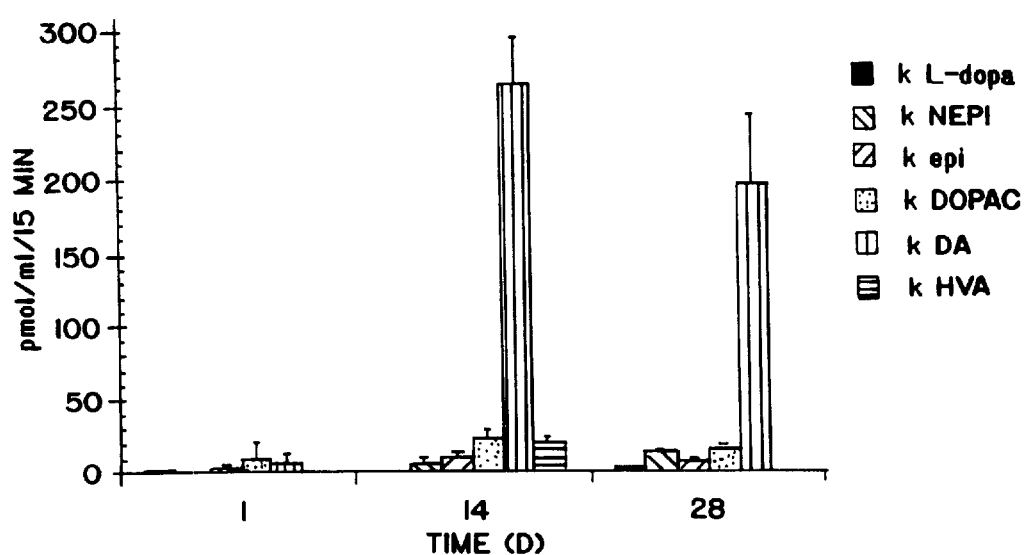
Figure 5A:
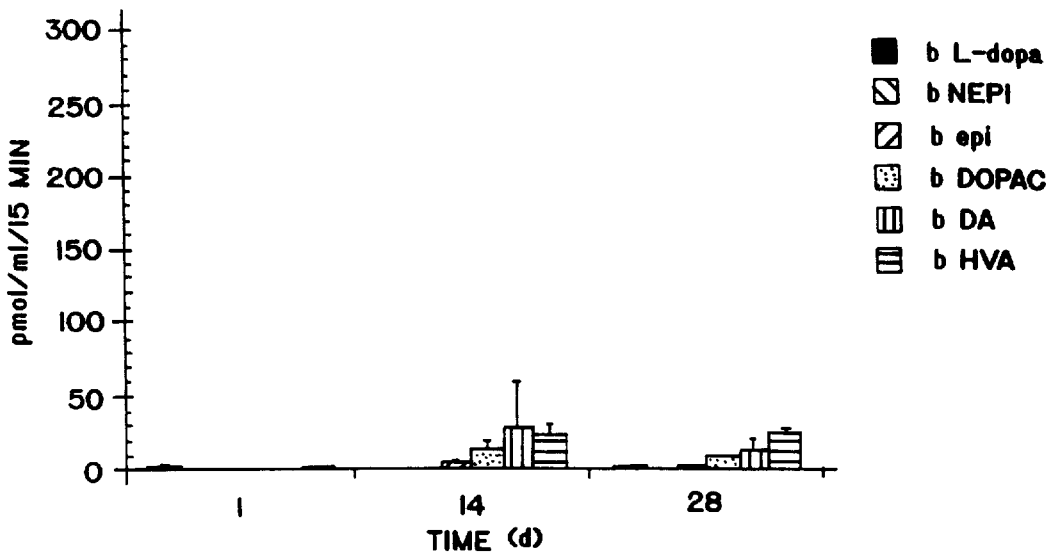
FIG. 5A and 5B show release of catecholamines from PC12A cells at 1, 14 and 28 days after encapsulation in BAOs having a inert PHEMA/MMA scaffold.
Figure 5B:
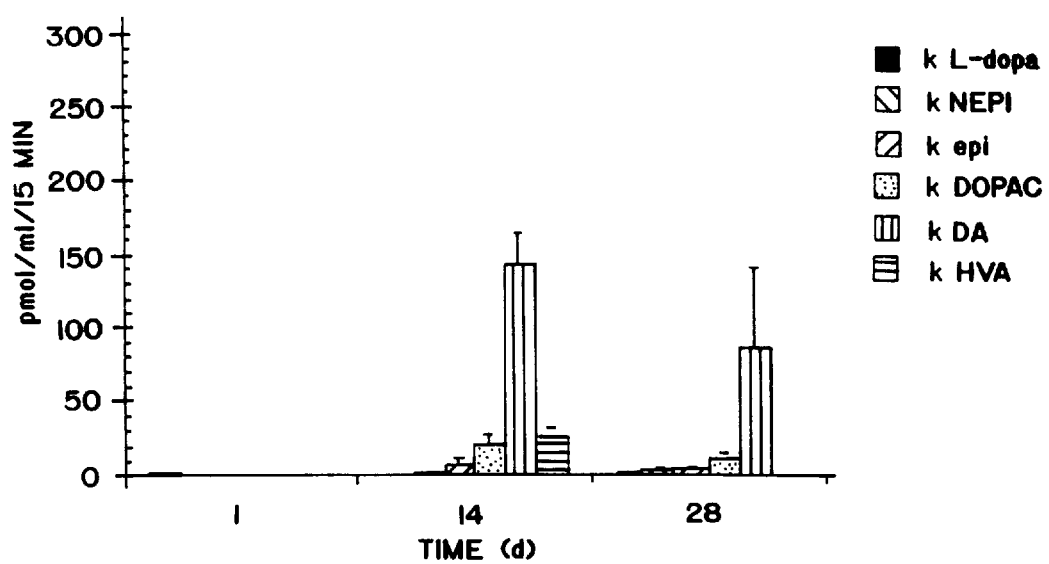
Figure 6:
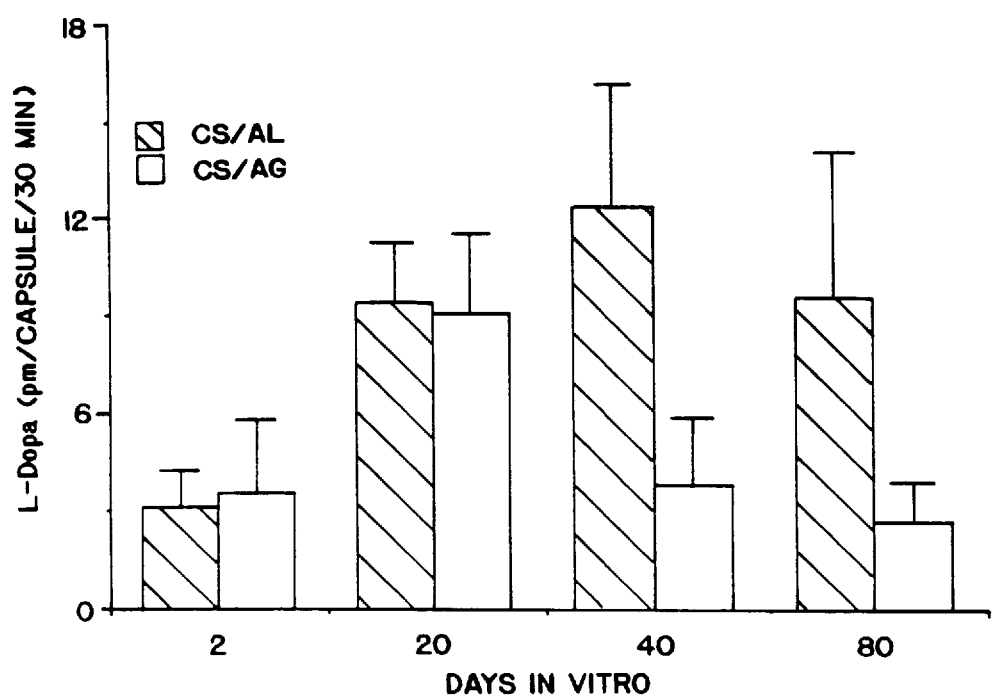
FIG. 6 shows release of L-dopa from SV40/Dβ4-NGF cells grown on Cultisphers™ in the presence of an alginate matrix (legend: CS/AL) or in the presence of an agarose matrix (legend: CS/AG) at 2, 20, 40 and 80 days after encapsulation in BAOs.

PC12A cells ($1\times10^7$ cells/ml) in HL-1 medium were injected into the lumens of the fibers, and the fibers heat sealed to produce BAOs approximately 1 cm long. The devices were held at 37° C. at ambient pressures in HL-1 media. To assess functionality of the encapsulated cells, the BAOs were tested for basal and $K^+$-evoked catecholamine release at 1, 14 and 28 days. The results are shown in FIGS. 4A and 5A (basal release) and FIGS. 4B and 5B ($K^+$-evoked release). These results show that PC12 cells encapsulated in BAOs having inert PHEMA and PHEMA/MMA scaffolds retain their functionality, as measured by catecholamine release.

Cell distribution in the BAOs was evaluated after 5 hours and 4 days by vertically cutting the fibers in half, and staining the cells with FDA/PI. These results indicated that PHEMA and PHEMA/MMA scaffolds are nontoxic and support cell viability and functionality of PC12 cells.

Example 15

Use of an NWPF to Promote Cell Adhesion and Differentiation in a BAO.

Six types of NWPF (Reemay, Tenn.) were tried: #2470, #2295, #2024, #2055, #2033, #2250 (Reemay #s). The fabric received was in flatsheet form: discs were punched out to fit into 24 well plates. The NWPF discs were immersed in 1% sodium dodecyl sulphate (SDS), w/v for 6 h and then rinsed with water (3 times). The discs were then immersed in 1% sulfuric acid (v/v in $H_2O$) for 13 h (overnight) and then rinsed 3 times with water. The discs dried on a paper towel and then sterilized by autoclaving.

The discs were cultured with 3 cell types to test for cell adhesion: BHK, AT-3, and TSA cells. Approximately 100,000 cells were added to a 24 well plate containing one of the above 6 NWPF discs in PC1 media. A serum-free medium was used to test for cell adhesion without the inference of serum (except for TSA cells). After 4 days, the BHK and AT-3 cells were examined for adhesion by PDA/PI. The cells had an elongated morphology and appeared to adhere on Reemay #2250, and 2055. At 10 days, BHK were growing best on #2250. AT-3 cells best adhered to 2024 and 2295. AT-3 cells grew best on 2024 at 10 days. TSA cells (in 10% FCS) after 1 day had an elongated morphology when grown on #2250, #2055, and grew best on #2024. At 7 days, TSA cells were growing best on #2055.

Example 16

SV40/DβH-NGF Cells on Microcarriers Suspended in Matrix Material

Regulatory elements of the dopamine β-hydroxylase (DβH) gene (Hoyle et al., *J. Neurosci.*, 14, pp. 2455–63 (1994)) were utilized to direct the coexpression of the SV40 T-antigen (tsa58) (DβH-SV) and human growth factor (DβH-hNGF) in transgenic mice. Coexpression of the chimeric genes resulted in neoplasms in the adrenal medulla and noradrenergic sympathetic ganglia. A tumor of the celiac region from one of these mice was dissected and the tumor tissue was mechanically dissociated and placed in cell culture (DMEM, 10% FBS, 37 C, 5% $CO_2$). Two distinct cell types, large flat fibroblast-like cells and small phase-bright cells having extensive neurite processes, were present from the initial culture period. The small cells exhibited features of catecholaminergic neuron including immunoreactivity for neurofilament-L and -M and tyrosine hydroxylase. Immunoreactivity for the SV40 T-antigen was also present in these cells, in contrast to the fibroblast-like cells, which were negative for these markers. The cells were passaged weekly.

Cells were grown on an CultiSphers™ as described in Example 10, and were suspended in either an alginate (1.5%) or agarose (1%) matrix. In the case of the alginate matrix, the alginate was cross-linked by immersing the devices in a 1% aqueous calcium chloride solution for 5 minutes after encapsulation. The cells/Cultisphers™/matrix were loaded into PAN/PVC hollow fibers as described in Example 10.

The cell-loaded BAOs were maintained in serum-free medium conditions. At selected time intervals, devices were washed prior to 30 minute incubations in HBSS. The basal medium was collected and assayed by HPLC-ED for L-dopa. The devices continued to secrete L-dopa at 80 days in vitro.

Example 17

Genetically Modified Myoblasts Secrete NGF After Differentiation

Mouse $C_2C_{12}$ myoblast cells have the advantage of being rapidly dividing cells, can be grown in large quantity in vitro, transferred to express proteins and selected clones can be isolated. Mouse $C_2C_{12}$ cells can be differentiated into a post-mitotic state upon exposure to low serum containing medium. These cells are thus advantageous for encapsulation in comparison to dividing cells whose proliferation cannot be controlled—the latter cells continue to divide until they fill the capsule and an accumulation of debris is observed after several months.

We tested the ability of a transfected $C_2C_{12}$ myoblast line to continue secreting hNGF after fusion into myotubes has taken place.

$C_2C_{12}$ myoblast cells (ATCC) were transfected with a hNGF gene, using the Lipofectamine reagent following the manufacturer's protocol (Gibco). Cells were selected in 1 mg G418 for 2 weeks and then tested for NGF output. Cells were plated at about 260 cells/cm2 in T75 flasks and 24 well plates with or without cover slips. Cells were fed twice a week with DMEM and 10% FBS. Cells were harvested at 1, 5, 8, and 13 days, at which time NGF secretion was measured. The results are shown in Table 2.

TABLE 2

Time Course of $C_2C_{12}$ screening For NGF Secretion

| cell line secretion | time in culture | % confluency | % fusion | NGF |
|---|---|---|---|---|
| parent | day 1 3/23/95 | 25 | 0 | nt |
| +NGF | day 1 3/23/95 | 25 | 0 | nt |
| parent | day 5 | 40 | 0 | nt |
| +NGF | day 5 | 30 | 0 | nt |
| parent | day 8 | 98 | 5 | *** |
| +NGF | day 8 | 90 | 1 | 0.0018 |
| parent | day 13 | 1000 | 80 | ND |
| +NGF | day 13 | 100 | 50 | 0.014 |

% fusion = % myoblast cells forming into myotubes
+NGF indicates $C_2C_{12}$ cells transfected with hNGF gene
parent indicates untransfected $C_2C_{12}$ cells
NGF secretion measured in pg/ml/cell/24 hr.
nt = not tested
ND = not detected
*Day 8 Cells have increased in size, preparing for fusion.
*Day 8 More fusion in the culture dishes than in the T flasks (Flow cytometry done on flasks)

These results suggest that transfected myoblasts continue to secrete the desired heterologous product, i.e., NGF, after terminal differentiation into myotubes.

Example 18

Genetically Modified Myoblasts Secrete CNTF After Differentiation

We transfected mouse $C_2C_{12}$ myoblasts with the pNUT expression vector (Baetge et al., *Proc. Natl. Acad. Sci. USA*, 83, pp. 5454–58 (1986) containing the human CNTF gene. The level of expression of the hCNTF gene and the bioactivity of the factor were analyzed by Northern blot, Elisa assay, and ChAT activity on embryonic spinal cord motoneuron cultures. One $C_2C_{12}$ clone was found to secrete approximately 0.2 g CNTF/10 cells/day. The rate of secretion of hCNTF was not altered upon differentiation of $C_2C_{12}$ myoblasts. Finally, $C_2C_{12}$-hCNTF could rescue motoneurons from axotomy-induced cell death. Morphological study of the facial nuclei of newborn rates, 1 week after axotomy, indicated that only 13.4% of the facial motoneurons were retained in control animals whereas a continuous release of hCNTF resulted in 22.7% survival of the motoneurons.

We claim:

1. A method for controlling distribution of cells within an implantable bioartificial organ comprising the steps of:
   (a) transforming the cells with a proliferation-promoting gene operatively linked to a regulatable promoter wherein the regulatable promoter is activated in vitro to achieve expression of the proliferation-promoting gene, resulting in proliferation of the transformed cells in vitro; and
   (b) inserting the cells from (a) in a bioartificial organ and inactivating the regulatable promoter either before or after inserting the cells in the bioartificial organ such that expression of the proliferation-promoting gene is inhibited to reduce or stop proliferation of the cells in the bioartificial organ in vivo in a host.

2. The method according to claim 1, wherein the proliferation promoting gene is an oncogene.

3. The method according to claim 2, wherein the oncogene is selected from the group consisting of c-myc, v-mos, v-Ha-ras, SV40 early region and E1-A.

4. The method according to claim 1, wherein the regulatable promoter is selected from the group consisting of tetracycline-responsive promoters, interferon-responsive promoters, glucocorticoid-responsive promoters and retroviral long terminal repeat promoters.

5. The method according to claim 4, wherein the interferon-responsive promoter is the Mx1 promoter and the proliferation-promoting gene is SV40 early region.

6. The method of claim 1 further comprising the step of:
   (c) reactivating the regulatable promoter in vivo in the bioartificial organ such that expression of the proliferation-promoting gene is achieved, resulting in further proliferation of the cells in the bioartificial organ.

7. A method for controlling distribution of cells within an implantable bioartificial organ comprising the steps of:
   (a) transforming the cells with a proliferation-suppressing gene operatively linked to a regulatable promoter wherein the regulatable promoter is inactivated in vitro to inhibit expression of the proliferation-suppressing gene, resulting in proliferation of the transformed cells in vitro; and
   (b) inserting the cells from (a) in a bioartificial organ and activating the regulatable promoter either before or after inserting the cells in the bioartificial organ such that expression of the proliferation-suppressing gene occurs to reduce or stop proliferation of the cells in the bioartificial organ in vivo in a host.

8. The method according to claim 7, wherein the proliferation-suppressing gene is a tumor suppressor gene selected from the group consisting of the p53 gene and the RB gene.

9. A method for controlling distribution of cells within an implantable bioartificial organ comprising the steps of:
   (a) transforming the cells with a differentiation-inducing gene operatively linked to a regulatable promoter wherein the regulatable promoter is inactivated in vitro to inhibit expression of the differentiation-inducing gene, resulting in proliferation of the transformed cells invtro; and
   (b) inserting the cells from (a) in a bioartificial organ and activating the regulatable promoter either before or after inserting the cells in the bioartificial organ such that expression of the differentiation-inducing gene occurs to reduce or stop proliferation of the cells in the bioartificial organ in vivo in a host.

10. The method according to claim 9, wherein the differentiation-inducing gene is the high mobility group chromosomal protein 14.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Cys Asp Pro Gly Tyr Ile Gly Ser Arg
    1                         5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Gly Arg Gly Asp Ser Pro
1               5

( 2 ) INFORMATION FOR SEQ ID NO:3:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Cys Ser Arg Ala Arg Lys Gln Ala Ala Ser Ile Lys Val Ala Val Ser
1               5                           10                          15

Ala Asp Arg ( 2 ) INFORMATION FOR SEQ ID NO:4:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Gly Gly Gly Gly Gly
1               5